(12) United States Patent  
Gerster et al.

(10) Patent No.: US 8,105,504 B2
(45) Date of Patent: Jan. 31, 2012

(54) STABILIZATION OF ORGANIC MATERIALS

(75) Inventors: Michèle Gerster, Binningen (CH); Peter Nesvadba, Marly (CH)

(73) Assignee: BASF SE, Ludwigshafen (DE)

( * ) Notice: Subject to any disclaimer, the term of this patent is extended or adjusted under 35 U.S.C. 154(b) by 1151 days.

(21) Appl. No.: 11/660,534

(22) PCT Filed: Aug. 22, 2005

(86) PCT No.: PCT/EP2005/054112
§ 371 (c)(1),
(2), (4) Date: Feb. 16, 2007

(87) PCT Pub. No.: WO2006/024610
PCT Pub. Date: Mar. 9, 2006

(65) Prior Publication Data
US 2007/0257234 A1  Nov. 8, 2007

(30) Foreign Application Priority Data

Aug. 31, 2004 (EP) .................................... 04104158

(51) Int. Cl.
*C09K 15/06* (2006.01)
*C08L 55/00* (2006.01)
*C08G 61/06* (2006.01)
*C08G 61/08* (2006.01)
*C08G 61/02* (2006.01)

(52) U.S. Cl. ............ 252/407; 524/1; 524/543; 524/553; 540/1; 540/4; 540/12; 540/13; 540/31; 544/1; 544/2; 544/3; 544/63; 544/69; 544/172; 544/173; 544/175; 546/14; 548/440; 549/1; 549/4; 549/6; 549/12; 549/29; 549/60; 549/307; 549/310; 549/460; 549/462; 549/469; 549/472; 549/479; 528/354; 528/361; 525/413; 525/415

(58) Field of Classification Search .................. 540/1, 4, 540/12, 13, 31; 544/1, 2, 3, 63, 65, 68, 69, 544/172, 173, 175; 546/14; 548/440; 549/1, 549/4, 6, 12, 29, 60, 307, 310, 460, 462, 549/469, 472, 479; 528/354, 361; 525/413, 525/415; 252/407
See application file for complete search history.

(56) References Cited

U.S. PATENT DOCUMENTS

| 4,345,016 A | 8/1982 | Takahashi et al. ............ 430/214 |
| 5,516,920 A * | 5/1996 | Nesvadba et al. ............. 549/307 |
| 5,773,543 A | 6/1998 | Rizzardo |
| 2003/0149211 A1 | 8/2003 | Wilczek |

FOREIGN PATENT DOCUMENTS

| JP | 9510181 T | 10/1997 |
| WO | 80/01566 | 8/1980 |

* cited by examiner

*Primary Examiner* — James J Seidleck
*Assistant Examiner* — Deve E Valdez
(74) *Attorney, Agent, or Firm* — Tyler A. Stevenson

(57) ABSTRACT

Organic materials which possess outstanding stability to oxidative, thermal or light-induced degradation comprise as stabilizers at least one compound of the formula (I) wherein the general symbols are as defined in claim 1. The compounds of formula I are especially useful as stabilizers for protecting polymers and lubricants against oxidative, thermal or light-induced degradation and as scavengers for oxidized developer in color photographic material.

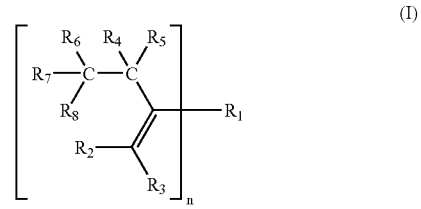

(I)

12 Claims, No Drawings

STABILIZATION OF ORGANIC MATERIALS

The present invention relates to compositions comprising an organic material, preferably a polymer or a lubricant, and to olefin derivatives, as well as to the use thereof for stabilizing organic materials against oxidative, thermal or light-induced degradation and to the use of the olefin derivatives as scavengers for the oxidized developer (also termed hereafter Dox scavengers) in color photographic material.

It is well known that one of the problems associated with color photography is the diffusion of the oxidized color developer away from the light sensitive silver halide emulsion layer in which it is formed into another silver halide emulsion layer, which can result in the formation of unwanted dyes at undesired places. For instance, while being generated in the green sensitive layer and forming a magenta dye through a coupling reaction with the incorporated magenta coupler, the oxidized developer can also diffuse to the red sensitive layer thereby producing unwanted cyan dye or to the blue sensitive layer thereby producing unwanted yellow dye. This kind of color formation in the wrong layers will damage the color balance of the photographic image and thus results in poor color reproduction. One way of circumventing this problem is to incorporate oxidized developer scavengers in interlayers between the light sensitive silver halide emulsion layers. These scavengers should have additional properties such as low tendency to migrate, good stability towards aerial oxidation and high solubility in photographic oils.

Hydroquinone derivatives which are useful as scavengers for oxidized developers are for example described in U.S. Pat. No. 4,345,016.

The use of some 3-phenyl-3H-benzofuran-2-ones as stabilizers for organic polymers is disclosed, inter alia in WO-A-80/01566 and U.S. Pat. No. 5,516,920.

The known stabilizers do not satisfy in every respect the high requirements which a stabilizer is required to meet, especially with regard to shelf life, water absorption, sensitivity to hydrolysis, in-process stabilization, color properties, volatility, migration behavior, compatibility and improvement in protection against light. As a result there continues to be a need for effective stabilizers for organic materials that are sensitive to oxidative, thermal and/or light-induced degradation.

It has now been found that a selected group of olefin derivatives is particularly suitable for use as stabilizers for organic materials that are susceptible to oxidative, thermal or light-induced degradation. These olefin derivatives are also particularly suitable as Dox scavengers in color photographic material.

Accordingly, the invention relates to a composition comprising
a) an organic material subject to oxidative, thermal or light-induced degradation, and
b) at least one compound of the formula I

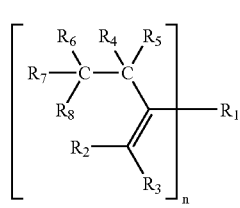

in which, if n is 1,
$R_1$ is

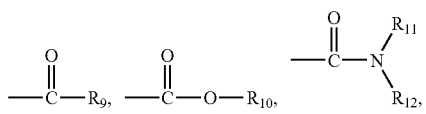

$-SOR_{10}$, $-SO_2R_{10}$, or $-CN$; or $R_1$ and $R_3$ form together

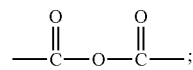

and
if n is 2,
$R_1$ is

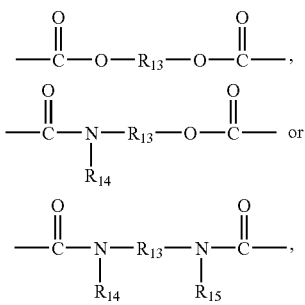

$R_2$ and $R_3$ independently of one another are hydrogen, $C_1$-$C_4$alkyl,

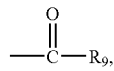

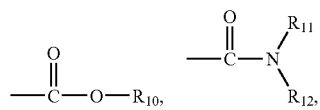

$-SOR_{10}$, $-SO_2R_{10}$, or $-CN$, with the proviso that at least $R_{12}$ one of $R_2$ or $R_3$ is hydrogen;
$R_4$ and $R_5$ independently of one another are hydrogen or $C_1$-$C_{25}$alkyl,
$R_6$, $R_7$ and $R_8$ independently of one another are hydrogen, $C_1$-$C_{25}$alkyl,

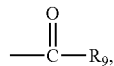

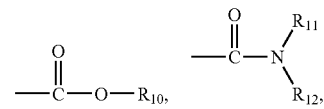, 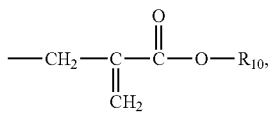

—SOR$_{10}$, —SO$_2$R$_{10}$, —CN,

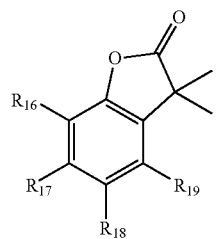

unsubstituted or C$_1$-C$_4$alkyl-substituted phenyl; or two of the radicals R$_6$, R$_7$ or R$_8$ form together with the carbon atom to which they are attached a radical of the formula Ia, Ib or Ic

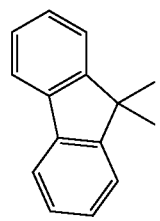  (Ia)

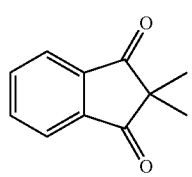  (Ib)

(Ic)

with the proviso that at least two of the radicals R$_6$, R$_7$ and R$_8$ are different from hydrogen, R$_9$ is hydrogen, C$_1$-C$_{25}$alkyl, C$_7$-C$_9$phenylalkyl, unsubstituted or C$_1$-C$_4$alkyl-substituted phenyl; unsubstituted or C$_1$-C$_4$alkyl-substituted C$_5$-C$_8$cycloalkyl;

R$_{10}$ is hydrogen, C$_1$-C$_{25}$alkyl, C$_7$-C$_9$phenylalkyl, unsubstituted or C$_1$-C$_4$alkyl-substituted phenyl; unsubstituted or C$_1$-C$_4$alkyl-substituted C$_5$-C$_8$cycloalkyl; or C$_3$-C$_{25}$alkyl which is interrupted by oxygen or sulfur;

R$_{11}$ and R$_{12}$ independently of one another are hydrogen, C$_1$-C$_{25}$alkyl, C$_7$-C$_9$phenylalkyl, unsubstituted or C$_1$-C$_4$alkyl-substituted phenyl; or R$_{11}$ and R$_{12}$, together with the nitrogen atom to which they are attached, form a 5-, 6- or 7-membered heterocyclic ring which is unsubstituted or is substituted by C$_1$-C$_4$alkyl or is interrupted by oxygen, sulfur or

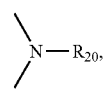

R$_{13}$ is C$_2$-C$_{18}$alkylene, C$_4$-C$_{18}$alkylene which is interrupted by oxygen, sulfur or

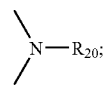

C$_2$-C$_{18}$alkenylene, C$_2$-C$_{20}$alkylidene, C$_7$-C$_{20}$phenylalkylidene, C$_5$-C$_8$cycloalkylene, C$_7$-C$_8$bicycloalkylene, unsubstituted or C$_1$-C$_4$alkyl-substituted phenylene; R$_{14}$ and R$_{15}$ independently of one another are hydrogen or C$_1$-C$_8$alkyl, R$_{16}$, R$_{17}$, R$_{18}$ and R$_{19}$ are each independently of one another hydrogen, chloro, hydroxyl, C$_1$-C$_{25}$alkyl, C$_7$-C$_9$phenylalkyl, unsubstituted or C$_1$-C$_4$alkyl-substituted phenyl; unsubstituted or C$_1$-C$_4$alkyl-substituted C$_5$-C$_8$cycloalkyl; C$_1$-C$_{18}$alkoxy, C$_1$-C$_{18}$alkylthio, C$_1$-C$_4$alkylamino, di-(C$_1$-C$_4$alkyl) amino, C$_1$-C$_{25}$alkanoyloxy, C$_1$-C$_{25}$alkanoylamino, C$_3$-C$_{25}$alkenoyloxy, C$_3$-C$_{25}$alkanoyloxy which is interrupted by oxygen, sulfur or

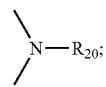

C$_6$-C$_9$cycloalkylcarbonyloxy, benzoyloxy or C$_1$-C$_{12}$alkyl-substituted benzoyloxy; or each pair of substituents R$_{16}$ and R$_{17}$ or R$_{17}$ and R$_{18}$ or R$_{18}$ and R$_{19}$ together with the linking carbon atoms, forms a benzene ring;

R$_{20}$ is hydrogen, C$_1$-C$_8$alkyl or benzyl, and n is 1 or 2.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

C$_1$-C$_4$Alkyl-substituted phenyl, which preferably contains 1 to 3, especially 1 or 2 alkyl groups, is, for example, o-, m- or p-methylphenyl, 2,3-dimethylphenyl, 2,4-dimethylphenyl, 2,5-dimethyl phenyl, 2,6-dimethyl phenyl, 3,4-dimethyl phenyl, 3,5-dimethyl phenyl, 2-methyl-6-ethylphenyl, 4-tert-butylphenyl, 2-ethylphenyl or 2,6-diethylphenyl.

C$_7$-C$_9$Phenylalkyl is, for example, benzyl, α-methylbenzyl, α,α-dimethylbenzyl or 2-phenylethyl.

Unsubstituted or C$_1$-C$_4$alkyl-substituted C$_5$-C$_8$cycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Preference is given to cyclohexyl and tert-butylcyclohexyl.

$C_3$-$C_{25}$Alkyl interrupted by oxygen or sulfur is, for example, $CH_3$—O—$CH_2CH_2$—, $CH_3$—S—$CH_2CH_2$—, $CH_3$—O—$CH_2CH_2$—O—$CH_2CH_2$—, $CH_3$—(O—$CH_2CH_2$—)$_2$O—$CH_2CH_2$—, $CH_3$—(O—$CH_2CH_2$—)$_3$O—$CH_2CH_2$— or $CH_3$—(O—$CH_2CH_2$—)$_4$O—$CH_2CH_2$—.

Where $R_{11}$ and $R_{12}$ together with the nitrogen atom to which they are attached, form a 5-, 6- or 7-membered heterocyclic ring which is unsubstituted or is substituted by $C_1$-$C_4$alkyl or is interrupted by oxygen, sulfur or

this denotes, for example, the following radicals:

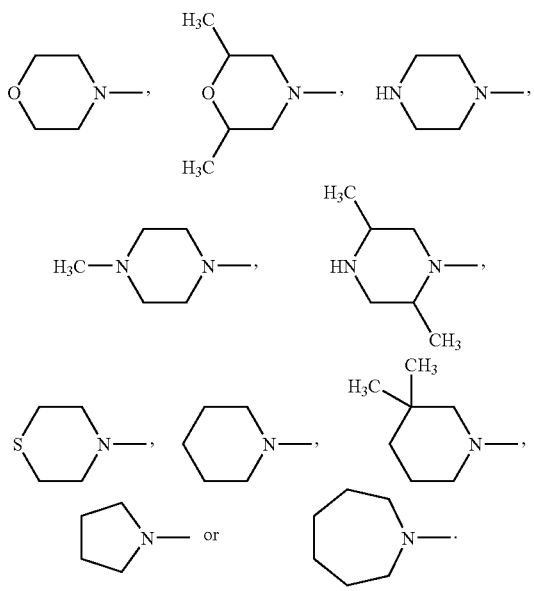

$R_{11}$ and $R_{12}$ preferably form with the nitrogen atom to which they are attached, a 6-membered heterocyclic ring interrupted by oxygen, such as, for example,

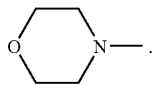

$C_2$-$C_{18}$Alkylene is a branched or unbranched radical, for example ethylene, propylene, trimethylene, tetramethylene, pentamethylene, hexamethylene, heptamethylene, octamethylene, decamethylene, dodecamethylene or octadecamethylene.

$C_4$-$C_{18}$Alkylene which is interrupted by oxygen, sulfur or

is, for example, —$CH_2CH_2$—O—$CH_2CH_2$—, —$CH_2CH_2$—S—$CH_2CH_2$—, —$CH_2CH_2$—NH—$CH_2CH_2$—, —$CH_2CH_2$—N($CH_3$)—$CH_2CH_2$—, —$CH_2CH_2$—O—$CH_2CH_2$—O—$CH_2CH_2$—, —$CH_2CH_2$—(O—$CH_2CH_2$—)$_2$—O—$CH_2CH_2$—, —$CH_2CH_2$—(O—$CH_2CH_2$—)$_3$O—$CH_2CH_2$—, —$CH_2CH_2$—(O—$CH_2CH_2$—)$_4$O—$CH_2CH_2$— or —$CH_2CH_2$—S—$CH_2CH_2$—.

$C_2$-$C_{18}$Alkenylene is, for example, vinylene, methylvinylene, octenylethylene or dodecenylethylene. Preference is given to $C_2$-$C_8$alkenylene.

Alkylidene having 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. Preference is given to $C_2$-$C_8$alkylidene.

Phenylalkylidene having 7 to 20 carbon atoms is, for example, benzylidene, 2-phenylethylidene or 1-phenyl-2-hexylidene. Preference is given to $C_7$-$C_9$phenylalkylidene.

$C_5$-$C_8$Cycloalkylene is a saturated hydrocarbon group having two free valencies and at least one ring unit and is, for example, cyclopentylene, cyclohexylene, cycloheptylene or cyclooctylene. Preference is given to cyclohexylene.

$C_7$-$C_8$Bicycloalkylene is, for example, bicycloheptylene or bicyclooctylene.

Unsubstituted or $C_1$-$C_4$alkyl-substituted phenylene is, for example, 1,2-, 1,3-, 1,4-phenylene. 1,4-Phenylene is preferred.

Alkoxy having up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having 1 to 12, especially 1 to 8, for example 1 to 6 carbon atoms.

Alkylthio having up to 18 carbon atoms is a branched or unbranched radical, for example methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. Preference is given to alkylthio having 1 to 12, especially 1 to 8, for example 1 to 6 carbon atoms.

Alkylamino having up to 4 carbon atoms is a branched or unbranched radical, for example methylamino, ethylamino, propylamino, isopropylamino, n-butylamino, isobutylamino or tert-butylamino.

Di($C_1$-$C_4$alkyl)amino also means that the two radicals independently of one another are branched or unbranched, for example dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or diisobutylamino.

Alkanoyloxy having up to 25 carbon atoms is a branched or unbranched radical, for example formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy. Preference is given to alkanoyloxy having 2 to 18, especially 2 to 12, for example 2 to 6 carbon atoms. Particular preference is given to acetoxy.

Alkanoylamino having up to 25 carbon atoms is a branched or unbranched radical, for example formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino or docosanoylamino. Preference is given to alkanoylamino having 2 to 18, especially 2 to 12, for example 2 to 6 carbon atoms.

Alkenoyloxy having 3 to 25 carbon atoms is a branched or unbranched radical, for example propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, iso-dodecenoyloxy, oleoyloxy, n-2-octadecenoyloxy or n-4-octadecenoyloxy. Preference is given to alkenoyloxy having 3 to 18, especially 3 to 12, for example 3 to 6, in particular 3 to 4 carbon atoms.

$C_3$-$C_{25}$Alkanoyloxy which is interrupted by oxygen, sulfur or

is, for example, $CH_3$—O—$CH_2$COO—, $CH_3$—S—$CH_2$COO—, $CH_3$—NH—$CH_2$COO—, $CH_3$—N($CH_3$)—$CH_2$COO—, $CH_3$—O—$CH_2CH_2$—O—$CH_2$COO—, $CH_3$—(O—$CH_2CH_2$—)$_2$O—$CH_2$COO—, $CH_3$—(O—$CH_2CH_2$—)$_3$O—$CH_2$COO— or $CH_3$—(O—$CH_2CH_2$—)$_4$O—$CH_2$COO—.

$C_6$-$C_9$cycloalkylcarbonyloxy is, for example, cyclohexylcarbonyloxy, cycloheptylcarbonyloxy or cyclooctylcarbonyloxy. Cyclohexylcarbonyloxy is preferred.

$C_1$-$C_{12}$Alkyl-substituted benzoyloxy, which preferably carries 1 to 3, especially 1 or 2 alkyl groups, is, for example, o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethyl benzoyloxy, 2-methyl-6-ethyl benzoyloxy, 4-tert-butylbenzoyloxy, 2-ethyl-benzoyloxy, 2,4,6-trimethyl benzoyloxy, 2,6-dimethyl-4-tert-butylbenzoyloxy or 3,5-di-tert-butylbenzoyloxy. Preferred substituents are $C_1$-$C_8$alkyl, especially $C_1$-$C_4$alkyl.

Compositions which are of interest include those comprising as component (b) a compound of the formula I, wherein, if n is 1, $R_1$ is

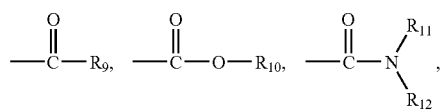

—$SOR_{10}$, —$SO_2R_{10}$, or —CN, and
if n is 2, $R_1$ is

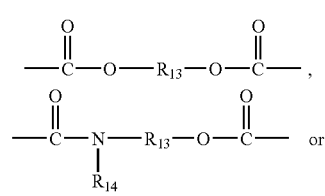

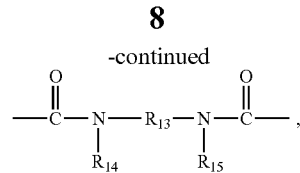

$R_2$ and $R_3$ independently of one another are hydrogen or $C_1$-$C_4$alkyl, with the proviso that at least one of $R_2$ or $R_3$ is hydrogen, $R_4$ and $R_5$ independently of one another are hydrogen or $C_1$-$C_{18}$alkyl, $R_6$, $R_7$ and $R_8$ independently of one another are hydrogen, $C_1$-$C_{18}$alkyl,

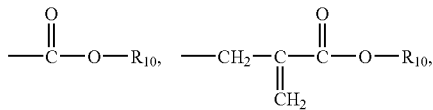

—CN, unsubstituted or $C_1$-$C_4$alkyl-substituted phenyl; or two of the radicals $R_6$, $R_7$ or $R_8$ form together with the carbon atom to which they are attached a radical of the formula Ia, Ib or Ic

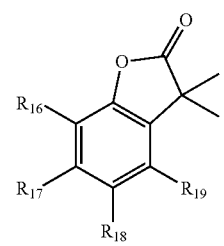 (Ia)

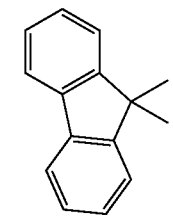 (Ib)

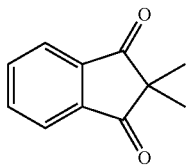 (Ic)

with the proviso that at least two of the radicals $R_6$, $R_7$ and $R_8$ are different from hydrogen, $R_9$ is hydrogen, $C_1$-$C_{18}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_7$cycloalkyl;

$R_{10}$ is hydrogen, $C_1$-$C_{18}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_7$cycloalkyl; or $C_3$-$C_{18}$alkyl which is interrupted by oxygen or sulfur;

$R_{11}$ and $R_{12}$ independently of one another are hydrogen, $C_1$-$C_{18}$alkyl, $C_7$-$C_9$phenylalkyl, unsubstituted or $C_1$-$C_4$alkyl-substituted phenyl; or $R_{11}$ and $R_{12}$, together with the nitrogen atom to which they are attached, form a 5- or 6-membered heterocyclic ring which is unsubstituted or is substituted by $C_1$-$C_4$alkyl or is interrupted by oxygen, sulfur or

$R_{13}$ is $C_2$-$C_{18}$alkylene, $C_4$-$C_{18}$alkylene which is interrupted by oxygen or sulfur; $C_2$-$C_{18}$alkenylene, $C_2$-$C_{18}$alkylidene, $C_7$-$C_{18}$phenylalkylidene, $C_5$-$C_7$cycloalkylene, unsubstituted or $C_1$-$C_4$alkyl-substituted phenylene;
$R_{14}$ and $R_{15}$ independently of one another are hydrogen or $C_1$-$C_8$alkyl,
$R_{16}$, $R_{17}$, $R_{18}$ and $R_{19}$ are each independently of one another hydrogen, $C_1$-$C_{18}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_7$cycloalkyl; $C_1$-$C_{18}$alkoxy, $C_1$-$C_{12}$alkylthio, $C_1$-$C_4$alkylamino, di-($C_1$-$C_4$alkyl)amino, $C_1$-$C_{18}$alkanoyloxy, $C_1$-$C_{18}$alkanoylamino, $C_3$-$C_{18}$alkenoyloxy, $C_3$-$C_{18}$alkanoyloxy which is interrupted by oxygen, sulfur or

$C_6$-$C_8$cycloalkylcarbonyloxy, benzoyloxy or $C_1$-$C_{12}$alkyl-substituted benzoyloxy; or each pair of substituents $R_{16}$ and $R_{17}$ or $R_{17}$ and $R_{18}$ or $R_{18}$ and $R_{19}$ together with the linking carbon atoms, forms a benzene ring;
$R_{20}$ is hydrogen, $C_1$-$C_8$alkyl or benzyl, and
n is 1 or 2.

Compositions that are of interest include those comprising as component (b) at least one compound of the formula I wherein $R_2$ and $R_3$ are hydrogen.

Preference is given to compositions comprising as component (b) at least one compound of the formula I wherein $R_4$ and $R_5$ are hydrogen.

Preference is also given to compositions comprising as component (b) at least one compound of the formula I wherein, if n is 1,
$R_1$ is

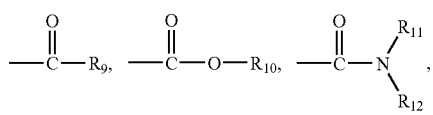

—$SOR_{10}$, —$SO_2R_{10}$, or —CN, and
if n is 2,
$R_1$ is

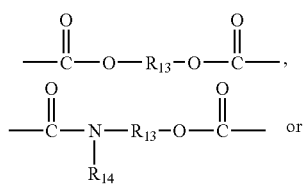

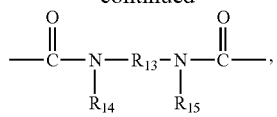

$R_2$ and $R_3$ independently of one another are hydrogen or methyl, with the proviso that at least one of $R_2$ or $R_3$ is hydrogen,
$R_4$ and $R_5$ independently of one another are hydrogen or $C_1$-$C_4$alkyl,
$R_6$, $R_7$ and $R_8$ independently of one another are hydrogen,

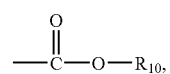

—CN, unsubstituted or $C_1$-$C_4$alkyl-substituted phenyl; or

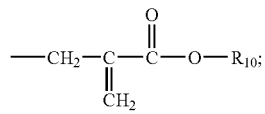

or two of the radicals $R_6$, $R_7$ or $R_8$ form together with the carbon atom to which they are attached a radical of the formula Ia, Ib or Ic

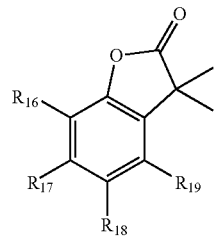

(Ia)

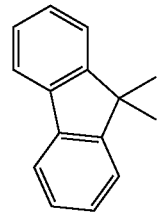

(Ib)

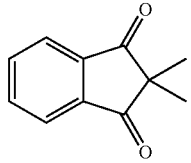

(Ic)

with the proviso that at least two of the radicals $R_6$, $R_7$ and $R_8$ are different from hydrogen,
$R_9$ is hydrogen, $C_1$-$C_8$alkyl, benzyl, phenyl or cyclohexyl,
$R_{10}$ is hydrogen, $C_1$-$C_{12}$alkyl, benzyl, phenyl or cyclohexyl,
$R_{11}$ and $R_{12}$ independently of one another are hydrogen, $C_1$-$C_{12}$alkyl, benzyl, phenyl; or $R_{11}$ and $R_{12}$, together with the nitrogen atom to which they are attached, form a 6-membered heterocyclic ring, $R_{13}$ is $C_2$-$C_{18}$alkylene, $C_4$-$C_{18}$alkylene which is interrupted by oxygen; cyclohexylene or phenylene, $R_{14}$ and $R_{15}$ independently of one another are hydrogen or $C_1$-$C_4$alkyl, $R_{16}$ is $C_1$-$C_{18}$alkyl, $C_7$-$C_9$phenylalkyl, phenyl or cyclohexyl, $R_{17}$ is hydrogen or methyl, $R_{18}$ is $C_1$-$C_{18}$alkyl, $C_7$-$C_9$phenylalkyl, phenyl or cyclohexyl, $R_{19}$ is hydrogen or methyl, and n is 1 or 2.

Preference is likewise given to compositions comprising as component (b) at least one compound of the formula I wherein, if n is 1, $R_1$ is, $$-\overset{O}{\underset{\|}{C}}-O-R_{10}, \quad -\overset{O}{\underset{\|}{C}}-N\overset{R_{11}}{\underset{R_{12}}{\diagup}},$$

—$SOR_{10}$, —$SO_2R_{10}$, or —CN, and if n is 2, $R_1$ is $$-\overset{O}{\underset{\|}{C}}-O-R_{13}-O-\overset{O}{\underset{\|}{C}}-,$$

$R_2$ and $R_3$ are hydrogen, $R_4$ and $R_5$ independently of one another are hydrogen or $C_1$-$C_4$alkyl, $R_6$, $R_7$ and $R_8$ independently of one another are hydrogen, $$-\overset{O}{\underset{\|}{C}}-O-R_{10},$$

—CN, unsubstituted or $C_1$-$C_4$alkyl-substituted phenyl; or $$-CH_2-\underset{\underset{CH_2}{\|}}{C}-\overset{O}{\underset{\|}{C}}-O-R_{10};$$

or two of the radicals $R_6$, $R_7$ or $R_8$ form together with the carbon atom to which they are attached a radical of the formula Ia, Ib or Ic (Ia)

[structure of benzofuranone with $R_{16}$, $R_{17}$, $R_{18}$, $R_{19}$ substituents and gem-dimethyl group]

(Ib)

[fluorene structure with gem-dimethyl group]

(Ic)

[2,2-dimethyl-indane-1,3-dione structure]

with the proviso that at least two of the radicals $R_6$, $R_7$ and $R_8$ are different from hydrogen, $R_{10}$ is hydrogen, $C_1$-$C_8$alkyl, benzyl, phenyl or cyclohexyl, $R_{11}$ and $R_{12}$ independently of one another are hydrogen, $C_1$-$C_{12}$alkyl, benzyl or phenyl, $R_{13}$ is $C_2$-$C_{12}$alkylene, $C_4$-$C_{12}$alkylene which is interrupted by oxygen; or phenylene, $R_{16}$ is $C_1$-$C_{12}$alkyl, phenyl or cyclohexyl, $R_{17}$ is hydrogen, $R_{18}$ is $C_1$-$C_{12}$alkyl, phenyl or cyclohexyl, $R_{19}$ is hydrogen, and n is 1 or 2.

Particular preference is given to compositions comprising as component (b) at least one compound of the formula I wherein, when n is 1, $R_1$ is $$-\overset{O}{\underset{\|}{C}}-O-R_{10},$$

—$SOR_{10}$ or —CN, and when n is 2, $R_1$ is $$-\overset{O}{\underset{\|}{C}}-O-R_{13}-O-\overset{O}{\underset{\|}{C}}-,$$

$R_2$ and $R_3$ are hydrogen, $R_4$ and $R_5$ are hydrogen, $R_6$, $R_7$ and $R_8$ independently of one another are hydrogen, $$-\overset{O}{\underset{\|}{C}}-O-R_{10}, \quad -CH_2-\underset{\underset{CH_2}{\|}}{C}-\overset{O}{\underset{\|}{C}}-O-R_{10},$$

—CN or phenyl; or two of the radicals $R_6$, $R_7$ or $R_8$ form together with the carbon atom to which they are attached a radical of the formula Ia, Ib or Ic

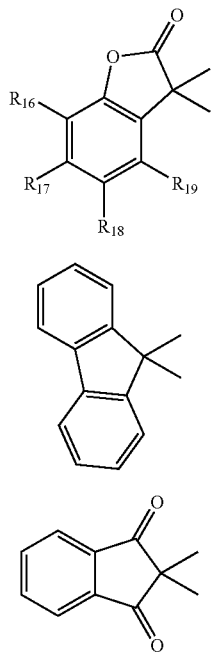

(Ia)

(Ib)

(Ic)

with the proviso that at least two of the radicals $R_6$, $R_7$ and $R_8$ are different from hydrogen,
$R_{10}$ is hydrogen, $C_1$-$C_4$alkyl, benzyl or phenyl,
$R_{13}$ is $C_2$-$C_8$alkylene or $C_4$-$C_8$alkylene which is interrupted by oxygen,
$R_{16}$ is $C_1$-$C_4$alkyl,
$R_{17}$ is hydrogen,
$R_{18}$ is $C_1$-$C_4$alkyl,
$R_{19}$ is hydrogen, and
n is 1 or 2.

The compounds of the formula I as component (b) in the novel composition are prepared for example by alkylation of a compound of the formula A with a compound of the formula B (A)

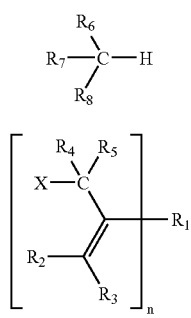

(B)

wherein the general symbols have the above meaning and X is a leaving group such as for example halogen, hydroxy or an esterified hydroxy group, in the presence of a base.

Halogen is preferably chloro, bromo or iodo.

An esterified hydroxy group is preferably an carboxylate, such as for example acetate; tosylate or triflate.

Component (b) is suitable for stabilizing organic materials against oxidative, thermal or light-induced degradation. Examples of such materials are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the precedent paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III)chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly($\alpha$-methylstyrene).

6. Aromatic homopolymers and copolymers derived from vinyl aromatic monomers including styrene, $\alpha$-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are natural, semi-synthetic or, preferably, synthetic polymers.

Particularly referred organic materials are synthetic polymers, most preferably thermoplastic polymers. Especially preferred organic materials are polyacetals, polyolefins such as polypropylene or polyethylene, polyether/polyurethanes, polyesters such as polybutylene terephthalate, polycarbonates or vulcanisates.

To be singled out for special mention is the efficacy of the compounds of the formula I against oxidative or thermal degradation, especially under the action of heat which occurs during the processing of thermoplasts. The compounds of the formula I of this invention are therefore admirably suited for use as processing stabilizers.

Component (b) will preferably be added to the organic material to be stabilized in concentrations of from 0.0005 to 10%, preferably 0.001 to 2%, typically 0.01 to 2%, based on the weight of said material [component (a)].

Component (b) is likewise used for polyurethane production, especially for preparing flexible polyurethane foams. In this context the novel compositions and the products produced therefrom are effectively protected against degradation. In particular, scorching during foam production is avoided.

The polyurethanes are obtained, for example, by reacting polyethers, polyesters and polybutadienes which contain terminal hydroxyl groups with aliphatic or aromatic polyisocyanates.

Polyethers having terminal hydroxyl groups are known and are prepared, for example, by polymerizing epoxides such as ethylene oxide, propylene oxide, butylene oxide, tetrahydrofuran, styrene oxide or epichlorohydrin with themselves, for example in the presence of $BF_3$, or by addition reaction of these epoxides, alone or as a mixture or in succession, with starting components containing reactive hydrogen atoms, such as water, alcohols, ammonia or amines, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many cases preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

These compounds generally have molecular weights of 400-10000 and are polyhydroxy compounds, especially compounds containing from two to eight hydroxyl groups, especially those of molecular weight from 800 to 10 000, preferably from 1000 to 6000, for example polyethers containing at least 2, generally 2 to 8, but preferably 2 to 4, hydroxyl groups, as are known per se for the preparation of homogeneous polyurethanes and cellular polyurethanes.

It is of course possible to employ mixtures of the above compounds containing at least two isocyanate-reactive hydrogen atoms, in particular with a molecular weight of 400-10 000.

Suitable polyisocyanates are aliphatic, cycloaliphatic, araliphatic, aromatic and heterocyclic polyisocyanates, for example ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3- and -1,4-diisocyanate and also any desired mixtures of these isomers, 1-isocyanato-3,3,5-trimethyl-5-isocyanatomethylcyclohexane, 2,4- and 2,6-hexahydrotolylene diisocyanate and also any desired mixtures of these isomers, hexahydro-1,3- and/or -1,4-phenylene diisocyanate, perhydro-2,4'- and/or -4,4'-diphenylmethanediisocyanate, 1,3- and 1,4-phenylene diisocyanate, 2,4- and 2,6-tolylene diisocyanate, and also any desired mixtures of these isomers, diphenylmethane 2,4'- and/or -4,4'-diisocyanate, naphthylene 1,5-diisocyanate, triphenylmethane 4,4',4"-triisocyanate, polyphenyl-polymethylene polyisocyanates as are obtained by aniline-formaldehyde condensation followed by phosgenization, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to employ the isocyanate group-containing distillation residues, as they are or dissolved in one or more of the abovementioned polyisocyanates, which are obtained in the course of the industrial preparation of isocyanates. It is additionally possible to use any desired mixtures of the abovementioned polyisocyanates.

Particular preference is given in general to the polyisocyanates which are readily obtainable industrially, for example 2,4- and 2,6-tolylene diisocyanate and any desired mixtures of these isomers ("TDI"), polyphenyl-polymethylene-polyisocyanates as prepared by aniline-formaldehyde condensation followed by phosgenization ("crude MDI"), and polyisocyanates containing carbodiimide, urethane, allophanate, isocyanurate, urea or biuret groups ("modified polyisocyanates").

Component (b) is also suitable for stabilizing polyolefins which are in long-term contact with extracting media.

In addition to components (a) and (b) the novel compositions may comprise further costabilizers (additives), typically the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutyl phenol, 2,6-dicyclopentyl-4-methyl phenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethyl phenol, 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methyl phenol), 4,4'-thiobis(3,6-di-sec-amyl phenol), 4,4'-bis(2,6-dimethyl-4-hydroxyphenyl)disulfide.

1.6. Alkylidenebisphenols, for example 2, 2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methyl phenol, 1,1,3-tris(5-tert-butyl-4-hydroxy-2-methyl phenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methyl phenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1, 5,5-tetra(5-tert-butyl-4-hydroxy-2-methyl phenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethyl benzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecyl mercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1, 3,5-tris(3,5-di-tert-butyl-4-hydroxybenzyl)-2,4,6-trimethylbenzene, 1,4-bis(3,5-di-tert-butyl-4-hydroxybenzyl)-2,3,5, 6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3, 5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo

[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5,5]undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenyl methane, 1,2-bis[(2-methyl phenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N N-bis(2,2,6,6-tetramethylpiperid-4-yl-hexamethylenediamine, bis(2,2,6,6-tetramethyl piperid-4-yl)sebacate, 2,2,6,6-tetramethyl piperidin-4-one, 2,2,6,6-tetramethylpiperidin-4-ol.

2. UV Absorbers and light stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenyl benzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-yl phenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butyl phenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4- piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl)n-butyl-3,5-di-tert-butyl-4-hydroxybenzyl malonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4,5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1, 3,5-triazine, 2-{2-hydroxy-4-[3-(2-ethylhexyl-1-oxy)-2-hydroxypropyloxy]phenyl}-4,6-bis-(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-, 1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzyl hydroxylamine, N,N-diethyl hydroxylamine, N,N-dioctylhydroxylamine, N,N-dilaurylhydroxylamine, N,N-ditetradecyl hydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(p-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1, 3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butyl benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)-benzofuran-2-one], 5,7-di-tert-butyl-3-(4-ethoxyphenyl)benzofuran-2-one, 3-(4-acetoxy-3,5-dimethylphenyl)-5,7-di-tert-butyl benzofuran-2-one, 3-(3,5-dimethyl-4-pivaloyloxyphenyl)-5,7-di-tert-butyl benzofuran-2-one, 3-(3,4-dimethylphenyl)-5,7-di-tert-butyl benzofuran-2-one, 3-(2,3-dimethylphenyl)-5,7-di-tert-butyl benzofuran-2-one, 3-(2-acetyl-5-isooctyl phenyl)-5-isooctyl benzofuran-2-one.

The costabilizers are added, for example, in concentrations of from 0.01 to 10%, based on the overall weight of the organic material to be stabilized.

The compounds of the formula I can be used in particular together with phenolic antioxidants, light stabilizers and/or processing stabilizers.

Other preferred compositions comprise, in addition to compounds of the formula I, a compound of the organic phosphite or phosphonite type.

The fillers and reinforcing agents (item 12 in the list), for example talc, calcium carbonate, mica or kaolin, are added to the polyolefin in concentrations, for example, of from 0.01 to 40%, based on the organic material to be stabilized.

Further preferred compositions comprise in addition to components (a) and (b) further additives as well, especially alkaline earth metal salts of higher fatty acids, for example calcium stearate, calcium lactate and/or calcium stearoyl-2-lactylate.

As a conventional stabilizer combination for the processing of polymeric organic materials, such as, for example, polyolefins, into corresponding moulded articles, the combination of a phenolic antioxidant with a secondary antioxidant based on an organic phosphite or phosphonite is recommended. Depending on the substrate and process, however, many polyolefin processors are obliged to operate processes in the high-temperature range above approx. 280° C. The inclusion of a processing stabilizer of the formula I is particularly suitable for high-temperature applications, especially in the temperature range above 300° C. Technical materials and moulded articles for instance based on HD polyethylene, such as, for example, pipes and their technical variants (fittings), can be manufactured with a higher output and fewer rejects. A further advantage of the compounds of the formula I is also that they can be used in a very small amount, which results in a reduction in the overall antioxidant concentration compared with conventional stabilizer mixtures. For instance the use of a low concentration of a compound of the formula I allows the overall stabilizer concentration to be reduced by approximately a third in, for example, polyolefins, which at the same time represents an economic advantage.

The compounds of the formula I and other optional additives are incorporated into the organic polymeric material according to known methods, for example before or during shaping to moulded articles or alternatively by coating the organic polymeric material with a solution or dispersion of the compounds and subsequently evaporating the solvent. The compounds of the formula I can also be added to the materials to be stabilized in the form of a master batch which contains these compounds, typically in a concentration of, for example, from 2.5 to 25% by weight.

The compounds of the formula I may also be added before or during polymerization or before crosslinking.

In this connection, particular attention is drawn to the surprising feature that the novel compounds of the formula I inhibit discoloration, especially so-called pinking in the manufacture of e.g. polyurethane foams.

The compounds of the formula I, and where applicable further additives, may be incorporated into the material to be stabilized in pure form or encapsulated in waxes, oils or polymers.

The compounds of the formula I, and where applicable further additives, may also be sprayed onto the polymer to be stabilized. They are able to be used to dilute other additives (e.g. the above-mentioned conventional additives) or melts thereof, so that they can also be sprayed together with these additives onto the polymer to be stabilized. Application by spraying during the deactivation of the polymerization catalysts is especially advantageous, in which case spraying is conveniently effected with the vapour used for deactivation.

The materials stabilized in this way can be employed in a wide variety of forms, for example as films, fibres, tapes, moulding compositions, profiles or as binders for coating materials, especially powder coatings, adhesives or putties.

The polyolefins stabilized in this way can likewise be employed in a wide variety of forms, especially as thick-layer polyolefin mouldings which are in long-term contact with extractive media, such as, for example pipes for liquids or gases, films, geomembranes, tapes, strips, profiles or tanks.

The preferred thick-layer polyolefin mouldings have a layer thickness of from 1 to 50 mm, in particular from 1 to 30 mm, for example from 2 to 10 mm.

Preference is given to a process for stabilizing polyolefins that are in long-term contact with extractive media, wherein the polyolefins are thick-layer polyolefin mouldings and have a layer thickness of from 1 to 50 mm, in particular from 1 to 30 mm, for example from 2 to 10 mm, which comprises incorporating in or applying to said polyolefins at least a compound of the formula I.

Also of particular interest is a process for stabilizing thick-layer polyolefin mouldings that are in long-term contact with extractive media, wherein the thick-layer polyolefin mouldings are pipes or geomembranes, which comprises incorporating in or applying to said mouldings at least a compound of the formula I.

The term geomembranes refers to films which are employed, for example, in landfill sites and are required to have a service life of up to 300 years.

Extractive media are, for example, liquid or gaseous inorganic or organic materials.

Examples of gaseous inorganic materials are oxygen; nitrogen; oxides of nitrogen; for example NO, laughing gas or $NO_2$; oxides of sulfur, for example sulfur dioxide; halogens, for example fluorine or chlorine; Brönstedt acids, for example hydrofluoric acid, hydrochloric acid, hydrobromic acid, hydroiodic acid or hydrocyanic acid; or bases, for example ammonia.

Examples of gaseous organic materials are $C_1$-$C_4$alkanes, for example methane, ethane, propane or butane; carbon monoxide; carbon dioxide; or phosgene.

Examples of liquid inorganic materials are water, chlorinated drinking water or aqueous salt solutions, for example sodium chloride solution (brine) or sodium sulfate solution; bromine; acid halides, e.g. titanium tetrachloride, thionyl chloride, nitrosyl chloride or trimethylsilyl chloride; alkalis, for example aqueous sodium hydroxide (NaOH), aqueous potassium hydroxide (KOH), aqueous ammonia solution, aqueous sodium bicarbonate solution or aqueous sodium carbonate solution.

Examples of liquid organic materials are organic solvents or liquid organic reagents.

Examples of organic solvents are aliphatic hydrocarbons, for example pentane, hexane, heptane, octane, petroleum spirit, nonane or decane; alcohols, for example methanol, ethanol, isopropanol, butanol, pentanol, amyl alcohol, cyclohexanol, pentaerythritol, ethylene glycol, ethylene diglycol, methylcellosolve, polyethylene glycol or glycerol; ketones, for example acetone, diethyl ketone, methyl ethyl ketone, diphenyl ketone or cyclohexanone; ethers, for example diethyl ether, dibutyl ether, tetrahydrofuran or dioxane; aromatic hydrocarbons, for example benzene, toluene or xylene; heterocyclic solvents, for example furan, pyridine, 2,6-lutidine or thiophene; dipolar aprotic solvents, for example dimethylformamide, diethylacetamide or acetonitrile; or surfactants.

For the purposes of the present invention, extractive media are also mixtures and solutions, especially aqueous mixtures, emulsions or solutions, of liquid or gaseous inorganic and organic materials as listed above.

Of particular interest are those extractive media which are important in the chemical industry or in landfill sites.

A preferred embodiment of the present invention is therefore also the use of a compound of the formula I, with or without further additives, for improving the stability of polyolefins that are in long-term contact with extractive media.

The preferred compounds of the formula I for the use as stabilizers and the process for stabilizing are the same as those described for the compositions with an organic material.

The compositions according to the invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sun-shields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Thus, a further embodiment of the present invention relates to a shaped article, in particular a film, pipe, profile, bottle, tank or container, fiber containing a composition as described above.

A further embodiment of the present invention relates to a molded article containing a composition as described above. The molding is in particular effected by injection, blow, compression, roto-molding or slush-molding or extrusion.

As already mentioned, the organic materials to be protected are preferably organic, especially synthetic, polymers. In this context, thermoplastic materials are protected with particular advantage. Attention should be drawn above all in this context to the outstanding activity of the stabilizers of the formula I as in-process stabilizers (heat stabilizers). For this purpose they are advantageously added to the polymer prior to or during its processing. However, other polymers too (for example elastomers) or lubricants or hydraulic fluids can be stabilized against degradation, for example light-induced or thermooxidative degradation. Elastomers can be taken from the above listing of possible organic materials.

The invention relates also to compositions comprising a functional fluid, preferably from the series of lubricants, hydraulic fluids and metal-working fluids and also fuels for powering engines of the 4-stroke, Otto, 2-stroke, diesel, Wankel and orbital types, and at least one compound of the formula I.

The compounds of the formula I may preferably be used in lubricants and fuels as multifunctional stabilizers, that is to say they combine in themselves antioxidative, friction-reducing, extreme-pressure-protection and wear-protection action and also anti-corrosion properties.

Preferred lubricants and fuels and related products are engine oils, turbine oils, gear oils, hydraulic fluids, diesel or Otto fuels, metal-working fluids and lubricating greases.

Especially preferred lubricants are mineral oils, synthetic oils or mixtures thereof.

Products known per se are used as functional fluids from the series of lubricants, hydraulic fluids and metal-working fluids.

The lubricants and hydraulic fluids that come into consideration will be familiar to the person skilled in the art and are described in the relevant specialist literature, such as, for example, in Dieter Klamann, "Schmierstoffe und verwandte Produkte" [Lubricants and related products] (Verlag Chemie, Weinheim, 1982), in Schewe-Kobek, "Das Schmiermittel-Taschenbuch" [The lubricant handbook] (Dr. Alfred Hüthig-Verlag, Heidelberg, 1974) and in "Ullmanns Enzyklopädie der technischen Chemie" [Ullmann's Encyclopaedia of Industrial Chemistry], Vol. 13, pages 85-94 (Verlag Chemie, Weinheim, 1977).

The lubricants are especially oils and greases, for example based on a mineral oil. Oils are preferred.

A further group of lubricants that may be used are vegetable or animal oils, greases, tallows and waxes or mixtures thereof with one another or mixtures with the mentioned mineral or synthetic oils.

Vegetable and animal oils, greases, tallows and waxes are, for example, palm-kernel oil, palm oil, olive oil, rapeseed oil, rape oil, linseed oil, groundnut oil, soybean oil, cottonseed oil, sunflower oil, pumpkin seed oil, coconut oil, maize oil, castor oil, tree nut oil and mixtures thereof, fish oils, tallows obtained from slaughtered animals, such as beef tallow, neatsfoot oil and bone oil, and modified, epoxidised and sulfoxidised forms thereof, for example epoxidised soybean oil.

The mineral oils are based especially on hydrocarbon compounds.

Examples of synthetic lubricants include lubricants based on aliphatic or aromatic carboxy esters, polymeric esters, polyalkylene oxides, phosphoric acid esters, poly-alpha-olefins or silicones, a diester of a divalent acid with a monohydric alcohol, such as, for example, dioctyl sebacate or dinonyl adipate, a triester of trimethylol propane with a monovalent acid or with a mixture of such acids, such as, for example, trimethylolpropane tripelargonate, trimethylolpropane tricaprylate or mixtures thereof, a tetraester of pentaerythritol with a monovalent acid or with a mixture of such acids, such as, for example, pentaerythritol tetracaprylate, or a complex ester of monovalent and divalent acids with polyhydric alcohols, for example a complex ester of trimethylolpropane with caprylic and sebacic acid, or a mixture thereof. Apart from mineral oils there are especially suitable, for example, poly-alpha-olefins, ester-based lubricants, phosphates, glycols, polyglycols and polyalkylene glycols, and also mixtures thereof with water.

Metal-working fluids and hydraulic fluids may be prepared on the basis of the same substances as those described above for the lubricants, such fluids frequently being emulsions of such substances in water or other liquids.

Lubricant and fuel compositions according to the invention are used, for example, in internal combustion engines, e.g. in motorised vehicles equipped with, for example, engines of the Otto, diesel, two-stroke, Wankel or orbital type.

The compounds of the formula I are readily soluble in lubricants and fuels, metal-working fluids and hydraulic fluids and are therefore especially suitable as additives for lubricants and fuels, metal-working fluids and hydraulic fluids.

As additives in lubricants, the compounds of the formula I are effective even in very small amounts. They are mixed in with the lubricants advantageously in an amount of from 0.01 to 5% by weight, preferably in an amount of from 0.05 to 3% by weight and very especially in an amount of from 0.1 to 2% by weight, in each case based on the lubricant.

The compounds of the formula I may be mixed in with the lubricants and fuels in a manner known per se. The compounds of the formula I are readily soluble, for example, in oils. It is also possible to prepare a so-called master batch, which may be diluted, as a function of use, with the appropriate lubricant or fuel to the concentrations suitable for use. In such cases concentrations above 1% by weight are possible.

The lubricants and fuels, metal-working fluids and hydraulic fluids may additionally comprise other additives that are added in order to improve their basic properties still further; such additives include: further antioxidants, metal passivators, rust inhibitors, viscosity index improvers, pour-point depressants, dispersants, detergents, coefficient of friction reducers, further extreme-pressure additives and anti-wear additives. Such further additives are added advantageously in an amount of from 0.01 to 5% by weight.

A number of such compounds can be found, for example, in the above list "1. Antioxidants", especially points 1.1 to 1.19. In addition, further additives may be mentioned by way of example:

Examples of Further Antioxidants

Aliphatic or aromatic phosphites, esters of thiodipropionic acid or thiodiacetic acid or salts of dithiocarbamic or dithiophosphoric acid, 2,2,12,12-tetramethyl-5,9-dihydroxy-3,7,11-trithiamidecane and 2,2,15,15-tetramethyl-5,12-dihydroxy-3,7,10,14-tetrathiahexadecane.

Examples of Metal Deactivators, e.g. for Copper, are:
a) Benzotriazoles and derivatives thereof, e.g. 2-mercaptobenzotriazole, 2,5-dimercaptobenzotriazole, 4- or 5-alkylbenzotriazoles (e.g. tolutriazole) and derivatives thereof, 4,5,6,7-tetrahydrobenzotriazole, 5,5'-methylenebis-benzotriazole; Mannich bases of benzotriazole or tolutriazole, such as 1-[di(2-ethylhexyl)aminomethyl]tolutriazole and 1-[di(2-ethylhexyl)aminomethyl]benzotriazole; alkoxyalkylbenzotriazoles, such as 1-(nonyloxymethyl)benzotriazole, 1-(1-butoxyethyl)benzotriazole and 1-(1-cyclohexyloxybutyl)tolutriazole.
b) 1,2,4-Triazoles and derivatives thereof, e.g. 3-alkyl- (or -aryl-)1,2,4-triazoles, Mannich bases of 1,2,4-triazoles, such as 1-[di(2-ethylhexyl)aminomethyl]-1,2,4-triazole; alkoxyalkyl-1,2,4-triazoles, such as 1-(1-butoxyethyl)-1,2,4-triazole; acylated 3-amino-1,2,4-triazoles.
c) Imidazole derivatives, e.g. 4,4'-methylenebis(2-undecyl-5-methyl)imidazole and bis[(N-methyl)imidazol-2-yl]carbinol-octyl ether.
d) Sulfur-containing heterocyclic compounds, e.g. 2-mercaptobenzothiazole, 2,5-dimercapto-1,3,4-thiadiazole, 2,5-dimercaptobenzothiadiazole and derivatives thereof; 3,5-bis[di(2-ethyl hexyl)aminomethyl]-1,3,4-thiadiazolin-2-one.
e) Amino compounds, e.g. salicylidene-propylenediamine, salicylaminoguanidine and salts thereof.

Examples of Rust Inhibitors are:
a) Organic acids, their esters, metal salts, amine salts and anhydrides, e.g. alkyl- and alkenyl-succinic acids and their partial esters with alcohols, diols or hydroxycarboxylic acids, partial amides of alkyl- and alkenyl-succinic acids, 4-nonylphenoxyacetic acid, alkoxy- and alkoxyethoxycarboxylic acids, such as dodecyloxyacetic acid, dodecyloxy-(ethoxy)acetic acid and amine salts thereof, and also N-oleoyl-sarcosine, sorbitan monooleate, lead naphthenate, alkenylsuccinic acid anhydrides, e.g. dodecenylsuccinic acid anhydride, 2-(2-carboxyethyl)-1-dodecyl-3-methylglycerol and salts thereof, especially sodium and triethanolamine salts thereof.
b) Nitrogen-containing compounds, e.g.:
   i. Primary, secondary or tertiary, aliphatic or cycloaliphatic amines and amine salts of organic and inorganic acids, e.g. oil-soluble alkylammonium carboxylates, and 1-[N,N-bis(2-hydroxyethyl)amino]-3-(4-nonylphenoxy)propan-2-ol.
   ii. Heterocyclic compounds, e.g.: substituted imidazolines and oxazolines, e.g. 2-heptadecenyl-1-(2-hydroxyethyl)-imidazoline.
c) Phosphorus-containing compounds, e.g.:
   Amine salts of phosphoric acid partial esters or phosphonic acid partial esters, zinc dialkyldithiophosphates.
d) Sulfur-containing compounds, e.g.:
   Barium dinonyinaphthalene sulfonates, calcium petroleum sulfonates, alkylthio-substituted aliphatic carboxylic acids, esters of aliphatic 2-sulfocarboxylic acids and salts thereof.

e) Glycerol derivatives, e.g.:
  Glycerol monooleate, 1-(alkylphenoxy)-3-(2-hydroxyethyl)glycerols, 1-(alkylphenoxy)-3-(2,3-dihydroxypropyl)glycerols, 2-carboxyalkyl-1,3-dialkylglycerols.

Examples of Viscosity Index Improvers are:
  Polyacrylates, polymethacrylates, vinyl pyrrolidone/methacrylate copolymers, polyvinyl pyrrolidones, polybutenes, olefin copolymers, styrene/acrylate copolymers, polyethers.

Examples of Pour-Point Depressants are:
  Poly(meth)acrylates, ethylene/vinyl acetate copolymer, alkylpolystyrenes, fumarate copolymers, alkylated naphthalene derivatives.

Examples of Dispersants/Surfactants are:
  Polybutenylsuccinic acid amides or imides, polybutenylphosphonic acid derivatives, basic magnesium, calcium and barium sulfonates and phenolates.

Examples of Extreme-Pressure and Anti-Wear Additives are:
  Sulfur- and/or phosphorus- and/or halogen-containing compounds, such as, for example, chlorinated paraffins, sulfurated olefins or vegetable oils (soybean/rape oil), alkyl- or aryl-di- or -tri-sulfides, zinc dialkyldithiophosphates, zinc dithiocarbamates such as zinc diamyldithiocarbamate, molybdenum dithioates such as molybdenum dithiocarbamates, triaryl phosphates such as tritolyl phosphate, tricresyl phosphate, phenyl phosphate isopropyl ester, amine salts of mono- or di-alkylphosphoric acids such as the amine salts of mono-/di-hexyl phosphate, amine salts of alkylphosphonic acids such as the amine salt of methylphosphonic acid, triaryl phosphites such as tris[nonylphenyl]phosphite, dialkyl phosphites such as dioctyl phosphite, triaryl monothiophosphates such as triphenyl thionophosphate or tris[isononylphenyl] thionophosphate or tert-butylated triphenyl thionophosphate, substituted trialkyl mono- or di-thiophosphates such as diisopropoxyphosphinothioyl)thio]propionate or butylene-1,3-bis [(diisobutoxyphosphinothioyl)propionate, trithiophosphates such as trithiophosphoric acid S,S,S-tris(isooctyl-2-acetates), amine salts of 3-hydroxy-1,3-thiaphosphetane-3-oxide, benzotriazoles or derivatives thereof such as bis(2-ethylhexyl)aminomethyltolutriazole, dithiocarbamates such as methylene-bis-dibutyldithiocarbamate, derivatives of 2-mercaptobenzothiazole such as 1-[N,N-bis(2-ethyl hexyl)aminomethyl]-2-mercapto-1H-1,3-benzothiazole, derivatives of 2,5-dimercapto-1,3,4-thiadiazole such as 2,5-bis(tert-nonyldithio)-1,3,4-thiadiazole.

Examples of Coefficient of Friction Reducers are:
  Lard oil, oleic acid, tallow, rape oil, sulfurated fats, amines. Further examples are given in EP-A-0 565 487.

Examples of Special Additives for Use in Water/Oil Metal-Working Fluids and Hydraulic Fluids are:
Emulsifiers: petroleum sulfonates, amines, such as polyoxyethylated fatty amines, non-ionic surface-active substances;
Buffers: alkanolamines;
Biocides: triazines, thiazolinones, tris-nitromethane, morpholine, sodium pyridenethol;
Speed improvers: calcium and barium sulfonates;

Examples of Fuel Additives:
  Fuel additives are described in Kirk-Othmer, Encyclopedia of Chemical Technology, Vol 12, 1994 and in this instance are essentially petrol and diesel additives:
Petrol: dyes, especially azo dyes;
Antioxidants: aminic, especially para-phenylenediamines, or phenolic, e.g. 2,6-di-tert-butylphenol, as described above;
Metal deactivators: especially N,N'-disalicylidene-1,2-propane, benzotriazole, EDTA;
Rust inhibitors: for example carboxylic acids, sulfonates, amines or amine salts;
Dispersants: e.g. esters, high-molecular-weight amines, Mannich bases, succinimides, borated succinimides;
Detergents: for example fatty acid amides, nonpolymeric amines, polybutene succinimides, polyether amines, low-molecular-weight amines, sulfonates, salicylic acid derivatives;
Demulsifiers: for example long-chain alcohols or phenols containing poly-ethylene or -butylene groups;
Antiknock agents: tetralkyl lead, manganese methylcyclopentadienyltricarbonyl;
Oxygen compounds: esters of vegetable oils, ethers, alcohols for improving burn behaviour;
Diesel: ignition improvers (cetane improvers), e.g. alkyl nitrates, ether nitrates, alkyl diglycol nitrates, organic peroxides;
Stabilizers for, especially, cracked diesel: amines and other N-containing compounds that act as radical traps.

Especially preferred further additives in lubricants are aminic antioxidants, especially mixtures of mono- and di-alkylated tert-butyl-/tert-octyl-diphenylamines.

The present invention relates also to the use of the components of the formula I for stabilizing organic materials against oxidative, thermal or light-induced degradation, especially as additives in lubricants and fuels, hydraulic fluids or metal-working fluids, preferably in hydraulic oils and gear oils. The use according to the invention includes protection of the metal components to be lubricated against mechanical attrition (wear protection) and corrosion protection activity and also antioxidation activity—with respect both to the lubricant and to the metal components.

The present invention accordingly relates also to a process for stabilizing an organic material against oxidative, thermal or light-induced degradation, which comprises incorporating therein or applying thereto said at least a compound of the formula I.

The photographic materials according to this invention comprise a support bearing at least one layer of a light-sensitive silver halide emulsion.

Examples of color photographic materials according to this invention are color negative films, color reversal films, color positive films, color photographic paper, color reversal photographic paper, color-sensitive materials for the dye diffusion transfer process or the silver dye bleach process.

Of especial interest is a color photographic recording material comprising, on a base, at least one blue-sensitive silver halide emulsion layer containing at least one yellow dye providing compound, at least one green-sensitive silver halide emulsion layer containing at least one magenta dye providing compound, at least one red-sensitive silver halide emulsion layer containing at least one cyan dye providing compound, and customary (non light sensitive) top layer(s) and interlayers separating the light-sensitive layers.

The layers of the color photographic material can be arranged in various orders as is well known in the art.

The compounds of the formula I can be contained in any of the layers of the photographic material, i.e. in any of the light sensitive silver halide emulsion layers or in a non light sensitive layer. For use as a Dox scavenger, the compound of the formula I is preferably contained in one or more non light sensitive layers. In this case, the light sensitive layers may contain a lower concentration of a compound of the formula I or none.

The compounds of the formula I are preferably incorporated in an interlayer, especially a non-photosensitive interlayer, adjacent to the green-sensitive layer containing a magenta coupler. Preferred color photographic materials within this invention are those wherein the magenta coupler is of the pyrazolo-azole type, e.g. as disclosed in U.S. Pat. No. 5,538,840, column 49, line 51, until column 69, line 27, and publications cited therein; this section of U.S. Pat. No. 5,538,840 is hereby incorporated by reference.

Also preferred is a color photographic material, wherein the silver halide emulsion contains at least 95 mol-% AgCl.

In general, the compounds of the formula I are contained in the photographic material in an amount from 10 to 1000 mg/m², especially from 30 to 500 mg/m².

The compounds of formula I can be milled with polymers (e.g. PVS, polyester, polyvinyl alcohol etc.) and placed in a layer thus preventing their migration to adjacent layers. Also, compounds of formula I containing a suitable functional group (e.g. ester, hydroxy) can be reacted with a polymer, e.g. a polyvinyl alcohol or polyester, in order to attach them chemically. This form will reduce their migrating tendency.

Typical bases for the photographic material include polymeric films and paper (including polymer-coated paper). Details regarding supports and other layers of color photographic recording materials can be found in Research Disclosure, Item 36544, September 1994.

Essential constituents of the photographic emulsion layers are binders, silver halide particles and color couplers. Details regarding the constituents of the light sensitive layers and other (non light sensitive) layers such as top layers and interlayers separating the silver halide emulsion layers can be found in Research Disclosure, Item 38957, September 1996.

The invention therefore also relates to a color photographic material comprising a compound of the formula I, and to the use of a compound of the formula I as an additive in a color photographic material.

The invention also pertains to a process for preventing migration of the oxidized developer in a color photographic material from one color sensitive layer to another by incorporating a compound of the formula I into said material.

The compounds of the formula I of present invention are of special advantage when incorporated into photographic materials containing magenta couplers of the pyrazolotriazole class.

Examples for especially suitable yellow, magenta and cyan couplers to be used in combination with compounds of the present invention are as given in U.S. Pat. No. 5,538,840, column 33, line 3, until column 73, line 34, and publications cited therein. These passages are hereby incorporated by reference.

The compounds of the formula I which can be used in the context of this invention can be incorporated into the color photographic recording material, on their own or together with the color coupler and with or without further additives, by pre-dissolving them in high-boiling organic solvents. Preference is given to the use of solvents which boil at higher than 160° C. Typical examples of these solvents are the esters of phthalic acid, phosphoric acid, citric acid, benzoic acid or of fatty acids, and also alkylamides and phenols.

Further details on the structure of the color photographic material of the invention, and the components or further additives which can be employed in the novel material, can be found, inter alia, in U.S. Pat. No. 5,538,840, column 27, line 25, to column 33, line 2; and further in U.S. Pat. No. 5,538,840 from column 74, line 18, to column 106, line 16; and in U.S. Pat. No. 5,780,625, column 12, line 6, until column 57, line 6, and the publications cited in these 2 references; these passages of U.S. Pat. No. 5,538,840 and U.S. Pat. No. 5,780,625 are hereby incorporated by reference. Other useful information, how compounds of the formula I can be used in photographic material, can be taken from EP-A-0 871 066, page 10, line 10, until page 11, line 32, especially the references cited therein.

The photographic layers in the material of this invention may also include UV absorbers, which screen out the UV light and therefore protect the dyes, the couplers or other components against photodegradation. Hydroquinone compounds according to this invention may be contained in those layers where UV absorbers are present.

UV absorbers preferably to be used in the novel material or within the process of present invention include benzotriazoles, 2-hydroxybenzophenones, oxanilides, cyanoacrylates, salicylic esters, acrylonitrile derivatives, thiazolines and 2-hydroxyphenyltriazines.

GB-A-2,319,523 describes from page 49, line 21, until page 73, line 2, further details of the color photographic material, especially couplers (page 52, line 1, until page 56, line 22), UV absorbers (page 56, line 25, until page 68, line 1) and dark stabilizers (page 68, line 2, until page 73, line 2). Preferred UV absorbers of the 2-hydroxyphenyltriazine class are also described in detail, for example, in U.S. Pat. No. 5,668,200, column 1, line 30, until column 7, line 55, and as specific examples from column 26, line 31, until column 32, last line, and, together with some advantageous UV absorbers of the benzotriazole class, in U.S. Pat. No. 5,300,414, column 2 to column 10, line 54. These sections of U.S. Pat. No. 5,668,200 and U.S. Pat. No. 5,300,414 are hereby incorporated by reference.

The compounds of formula I may be used in combination with any known Dox scavengers such as hydrazines, hydrazides, hydroquinones of e.g. formula HQ-1 or HQ-2; 6-hydroxychromanes of e.g. formula A-3, or hydroxylamines of e.g. formula A-4

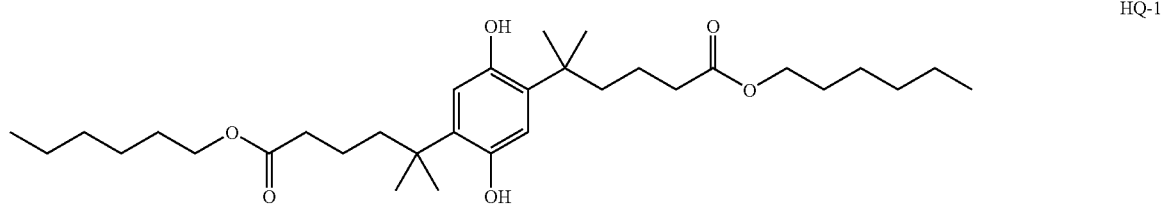

HQ-1

HQ-2

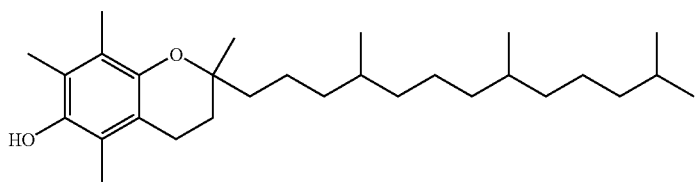

A-3

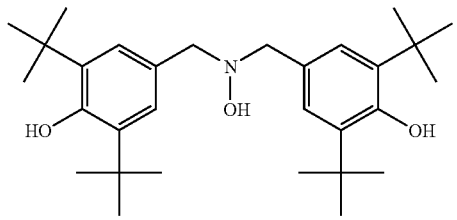

A-4

As silver halide emulsions it is possible to use customary silver chloride, silver bromide or silver iodide emulsions or mixtures thereof, such as silver chlorobromide and silver chloroiodide emulsions, in which the silver halides may have all known crystal forms. The use of silver chloride emulsions is accorded particular importance in the material of this novel process. The preparation of such emulsions and their sensitization are described in Research Disclosure, Item 307105, November 1989.

The compounds of the formula I may preferably also be used as stabilizers for ethylenically unsaturated resins against premature polymerization or crosslinking of the resins during transport or storage.

Preferred ethylenically unsaturated resins are for example liquid or resin-like monomers, oligomers, co-oligomers, polymers of co-polymers or mixtures thereof, which possess at least one ethylenically unsaturated bond and which are photo-polymerisable or curable with UV light.

The present invention also relates to new compounds of the formula I'

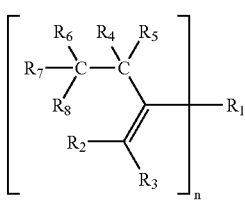

(I')

in which, if n is 1, $R_1$ is

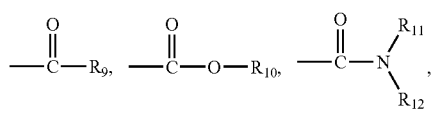

—$SOR_{10}$, —$SO_2R_{10}$, or —CN; or $R_1$ and $R_3$ form together

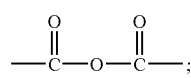

and
if n is 2,
$R_1$ is

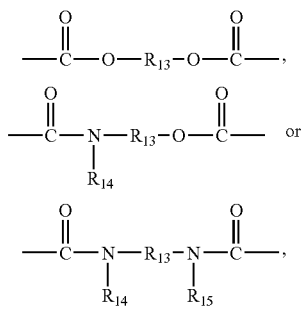

$R_2$ and $R_3$ independently of one another are hydrogen, $C_1$-$C_4$alkyl,

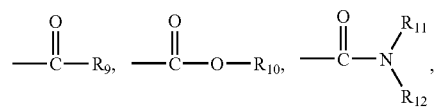

—$SOR_{10}$, —$SO_2R_{10}$, or —CN, with the proviso that at least one of $R_2$ or $R_3$ is hydrogen;

$R_4$ and $R_5$ independently of one another are hydrogen or $C_1$-$C_{25}$alkyl, two of the radicals $R_6$, $R_7$ or $R_8$ form together with the carbon atom to which they are attached a radical of the formula Ia, Ib or Ic

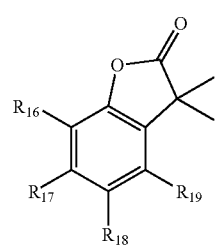

(Ia)

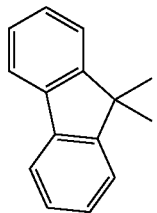
(Ib)

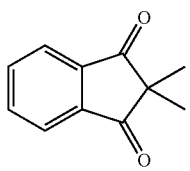
(Ic)

and the other radical $R_6$, $R_7$ or $R_8$ is hydrogen, $C_1$-$C_{25}$alkyl, unsubstituted or $C_1$-$C_4$alkyl-substituted phenyl, $R_9$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;

$R_{10}$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{25}$alkyl which is interrupted by oxygen or sulfur;

$R_{11}$ and $R_{12}$ independently of one another are hydrogen, $C_1$-$C_{25}$alkyl, $C_7$-$C_9$phenylalkyl, unsubstituted or $C_1$-$C_4$alkyl-substituted phenyl; or $R_{11}$ and $R_{12}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

$R_{13}$ is $C_2$-$C_{18}$alkylene, $C_4$-$C_{18}$alkylene which is interrupted by oxygen, sulfur or

$C_2$-$C_{18}$alkenylene, $C_2$-$C_{20}$alkylidene, $C_7$-$C_{20}$phenylalkylidene, $C_5$-$C_8$cycloalkylene, $C_7$-$C_8$bicycloalkylene, unsubstituted or $C_1$-$C_4$alkyl-substituted phenylene;

$R_{14}$ and $R_{15}$ independently of one another are hydrogen or $C_1$-$C_8$alkyl, $R_{16}$, $R_{17}$, $R_{18}$ and $R_{19}$ are each independently of one another hydrogen, chloro, hydroxyl, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; $C_1$-$C_{18}$alkoxy, $C_1$-$C_{18}$alkylthio, $C_1$-$C_4$alkylamino, di-($C_1$-$C_4$alkyl)amino, $C_1$-$C_{25}$alkanoyloxy, $C_1$-$C_{25}$alkanoylamino, $C_3$-$C_{25}$alkenoyloxy, $C_3$-$C_{25}$alkenoyloxy which is interrupted by oxygen, sulfur or

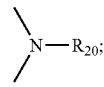

$C_6$-$C_9$cycloalkylcarbonyloxy, benzoyloxy or $C_1$-$C_{12}$alkyl-substituted benzoyloxy; or each pair of substituents $R_{16}$ and $R_{17}$ or $R_{17}$ and $R_{18}$ or $R_{18}$ and $R_{19}$ together with the linking carbon atoms, forms a benzene ring;

$R_{20}$ is hydrogen, $C_1$-$C_8$alkyl or benzyl, and n is 1 or 2.

The preferred general symbols are identical to those of the compound of the formula I.

Of very special interest are compounds of the formula I', wherein, when n is 1, $R_1$ is

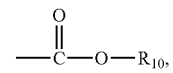

—$SOR_{10}$ or —CN, and
when n is 2,
$R_1$ is

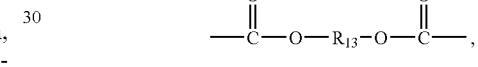

$R_2$ and $R_3$ are hydrogen,
$R_4$ and $R_5$ are hydrogen,
two of the radicals $R_6$, $R_7$ or $R_8$ form together with the carbon atom to which they are attached a radical of the formula Ia, Ib or Ic

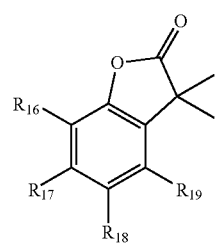
(Ia)

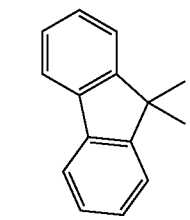
(Ib)

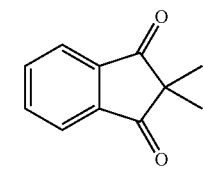
(Ic)

and the other radical $R_6$, $R_7$ or $R_8$ is hydrogen or phenyl, $R_{10}$ is hydrogen, $C_1$-$C_4$alkyl, benzyl or phenyl,
$R_{13}$ is $C_2$-$C_8$alkylene or $C_4$-$C_8$alkylene which is interrupted by oxygen,
$R_{16}$ is $C_1$-$C_4$alkyl,
$R_{17}$ is hydrogen,
$R_{18}$ is $C_1$-$C_4$alkyl,
$R_{19}$ is hydrogen, and
n is 1 or 2.

The examples which follow illustrate the invention in more detail. Parts and percentages are by weight.

EXAMPLE 1

Preparation of the Compound 101

Table 1

A mixture of 32.2 g (100 mmol) of 5,7-di-tert-butyl-3-phenyl-3H-benzofuran-2-one, 17.3 g (105 mmol) of 2-(bromomethyl)acrylic acid and 27.6 g (200 mmol) of potassium carbonate in 250 ml of acetone is heated under reflux for 5 hours. Thereafter, the acetone is evaporated under reduced pressure. Then 200 ml of water is added to the residue, the mixture is acidified (pH~3) with conc. HCl and extracted with ethylacetate (3×100 ml). The extracts are washed with water, dried over $Na_2SO_4$ and evaporated. The solid residue is suspended in 50 ml of hexane and filtered at 5° C. The filter cake is dried to afford 20.1 g (50%) of compound 101 (Table 1), off-white solid, m.p. 205-210° C. $^1$H-NMR ($^1$H 300 MHz, $CDCl_3$): δ=7.43-7.09 (m, 7 arom. H), 6.17 (s, 1H), 5.66 (s, 1H), 3.48-3.36 (dd, 2H), 1.35 (s, t-Bu), 1.24 (s, t-Bu).

EXAMPLE 2

Preparation of the Compound 102

Table 1

To a solution of 9.84 g (24.6 mmol) of 2-(5,7-di-tert-butyl-2-oxo-3-phenyl-2,3-dihydro-benzofuran-3-ylmethyl)-acrylic acid [compound 101 prepared according to Example 1], 5.17 g (25.0 mmol) of dicyclohexylcarbodiimide (DCC) and 100 mg (0.80 mmol) of 4-dimethylaminopyridine (DMAP) in 75 ml of dichloromethane is added 1.2 ml (29.0 mmol) of methanol and the mixture is stirred for 12 hours at room temperature. The white precipitate (dicyclohexylurea) is filtered off, the filtrate is evaporated and the residue is purified by flash chromatography on silica gel with dichloromethane to afford 7.35 g (71%) of compound 102 (Table 1), colorless resin. $^1$H-NMR ($^1$H 300 MHz, $CDCl_3$): δ=7.45-7.10 (m, 7 ArH), 6.03 (s, 1H), 5.55 (s, 1H), 3.53-3.39 (dd, 2H), 3.46 (s, $OCH_3$), 1.37 (s, t-Bu), 1.31 (s, t-Bu).

EXAMPLE 3

Preparation of the Compound 103

Table 1

To a solution of 10.0 g (25.0 mmol) of 2-(5,7-di-tert-butyl-2-oxo-3-phenyl-2,3-dihydrobenzofuran-3-ylmethyl)-acrylic acid [compound 101 prepared according to Example 1] in 80 ml of dichloromethane is added at room temperature 5.42 g (26.2 mmol) of dicyclohexylcarbodiimide (DCC), 305 mg (2.50 mmol) of dimethylaminopyridine (DMAP) and 1.8 ml (30.0 mmol) of ethanol. The reaction mixture is stirred at room temperature overnight. The solid is filtered off and the residue concentrated using a vacuum rotary evaporator. The crude material is purified by flash chromatography on silica gel with hexane/diethyl ether=20:1. The pure fractions give 9.32 g (87%) of compound 103 (Table 1), pale yellow solid, m.p. 76-78° C. $^1$H-NMR ($^1$H 300 MHz, $CDCl_3$): δ=7.70-7.45 (m, 6 arom. H), 7.33-7.20 (m, 1 arom. H), 6.24 (s, C=CHH), 5.75 (s, C=CHH), 4.20-4.05 (m, $OCH_2$), 3.73 (d, J=11.7 Hz, CHH—C=$CH_2$), 3.61 (d, J=13.2 Hz, CHH—C=$CH_2$), 1.59 (s, t-Bu), 1.53 (s, t-Bu), 1.30 (t, J=6.9 Hz, $OCH_2CH_3$). EI-MS: 434 ($M^+$).

EXAMPLE 4

Preparation of the Compound 104

Table 1

To a solution of 10.0 g (25.0 mmol) of 2-(5,7-di-tert-butyl-2-oxo-3-phenyl-2,3-dihydrobenzofuran-3-ylmethyl)-acrylic acid [compound 101 prepared according to Example 1] in 80 ml of dichloromethane is added at room temperature 5.42 g (26.2 mmol) of dicyclohexylcarbodiimide (DCC), 305 mg (2.50 mmol) of dimethylaminopyridine (DMAP) and 3.1 ml (30.0 mmol) of benzyl alcohol. The reaction mixture is stirred at room temperature overnight. The solid is filtered off and the residue concentrated using a vacuum rotary evaporator. The crude material is purified by flash chromatography on silica gel with hexane/diethyl ether=20:1. The pure fractions give 10.1 g (81%) of compound 104 (Table 1), white solid, m.p. 108-110° C. $^1$H-NMR ($^1$H 300 MHz, $CDCl_3$): δ=7.52-7.45 (m, 2 arom. H), 7.45-7.25 (m, 7 arom. H), 7.20-7.10 (m, 3 arom. H), 6.11 (s, C=CHH), 5.63 (s, C=CHH), 4.96-4.86 (m, $OCH_2Ph$), 3.60 (d, J=13.5 Hz, CHH—C=$CH_2$), 3.45 (d, J=13.2 Hz, CHH—C=$CH_2$), 1.40 (s, t-Bu), 1.34 (s, t-Bu). $^{13}$C-NMR (75 MHz, $CDCl_3$): 178.5 (s); 166.7 (s); 149.3 (s); 147.0 (s); 139.3 (s); 136.1 (s); 133.5 (s); 129.2 (d); 129.8 (t); 128.8 (d); 128.5 (d); 128.3 (d); 128.2 (s); 128.1 (d); 127.4 (d); 123.4 (d); 121.8 (d); 66.7 (t); 56.7 (s); 39.5 (t); 35.2 (s); 34.7 (s); 32.0 (q); 29.9 (q). EI-MS: 496 ($M^+$).

EXAMPLE 5

Preparation of the Compound 105

Table 1

To a solution of 10.0 g (25.0 mmol) of 2-(5,7-di-tert-butyl-2-oxo-3-phenyl-2,3-dihydrobenzofuran-3-ylmethyl)-acrylic acid [compound 101 prepared according to Example 1] in 80 ml of dichloromethane is added at room temperature 5.42 g (26.2 mmol) of dicyclohexylcarbodiimide (DCC), 305 mg (2.50 mmol) of dimethylaminopyridine (DMAP) and 2.8 ml (30.0 mmol) of n-butanol. The reaction mixture is stirred at room temperature overnight. The solid is filtered off and the residue concentrated using a vacuum rotary evaporator. The crude material is purified by flash chromatography on silica gel with hexane/diethyl ether=20:1. The pure fractions give 9.61 g (83%) of compound 105 (Table 1), colourless liquid. $^1$H-NMR ($^1$H 300 MHz, $CDCl_3$): δ=7.40-7.15 (m, 6 arom. H), 7.05-7.00 (m, 1 arom. H), 5.95 (s, C=CHH), 5.47 (s, C=CHH), 3.85-3.65 (m, $OCH_2$), 3.45 (d, J=13.2 Hz, CHH—C=$CH_2$), 3.31 (d, J=13.5 Hz, CHH—C=$CH_2$), 1.45-1.30 (m, $OCH_2CH_2$), 1.30 (s, t-Bu), 1.24 (s, t-Bu), 1.20-1.10 (m, $OCH_2CH_2CH_2$), 0.78 (t, J=7.2 Hz, $CH_3$). $^{13}$C-NMR (75 MHz, $CDCl_3$): 177.0 (s); 165.47 (s); 147.8 (s); 145.4 (s); 137.9 (s); 134.9 (s); 131.9 (s); 127.7 (d); 126.8 (t); 126.8 (d);

125.9 (d); 121.9 (d); 120.3 (s); 63.4 (t); 55.2 (s); 38.0 (t); 33.7 (s); 33.2 (s); 30.5 (q); 29.4 (t); 28.4 (q); 18.0 (t); 12.6 (q).

EXAMPLE 6

Preparation of the Compound 106

Table 1

A neat mixture of 1.50 g (3.45 mmol) of 2-(5,7-di-tert-butyl-2-oxo-3-phenyl-2,3-dihydro-benzofuran-3-ylmethyl)-acrylic acid ethyl ester [compound 103 prepared according to Example 3], 0.1 ml (1.73 mmol) of ethylene glycol and 42 mg (0.17 mmol) of dibutyltinoxide is heated up to 190° C. for 16 hours. After cooling to room temperature, the crude material is purified by flash chromatography on silica gel with hexane/diethyl ether=2:1. The pure fractions give 0.82 g (56%) of compound 106 (Table 1), white solid, m.p. 69-73° C. $^1$H-NMR ($^1$H 300 MHz, CDCl$_3$): δ=7.40-7.15 (m, 12 arom. H), 7.02-7.00 (m, 2 arom. H), 5.89 (d, J=2.4 Hz, C=CHH, 2H), 5.44 (s, C=CHH, 2H), 4.00-3.65 (m, OCH$_2$, 4H), 3.38 (d, J=13.5 Hz, CHH—C=CH$_2$, 2H), 3.31 (d, J=13.5 Hz, CHH—C=CH$_2$, 2H), 1.27 (s, t-Bu, 18H), 1.21 (s, t-Bu, 18H). $^{13}$C-NMR (75 MHz, CDCl$_3$): 176.7 (s); 170.4 (s); 164.7 (t); 147.6 (s); 145.4 (s); 137.6 (s); 134.1 (s); 131.9 (s); 127.5 (d); 126.7 (d); 126.6 (s); 125.7 (d); 121.7 (d); 120.0 (d); 119.9 (d); 60.9 (t); 60.8 (t); 54.9 (s); 37.9 (t); 33.6 (s); 33.0 (s); 30.4 (q); 28.3 (q). EI-MS: 838 (M$^+$).

EXAMPLE 7

Preparation of the Compound 107

Table 1

A neat mixture of 1.30 g (3.00 mmol) of 2-(5,7-di-tert-butyl-2-oxo-3-phenyl-2,3-dihydro-benzofuran-3-ylmethyl)-acrylic acid ethyl ester [compound 103 prepared according to Example 3], 0.18 g (1.50 mmol) of 1,6-hexanediol and few drops of Fascat 4200 is heated up to 150° C. for 24 hours. After cooling to room temperature, the crude material is purified by flash chromatography on silica gel with hexane/diethyl ether=4:1. The pure fractions give 0.67 g (50%) of compound 107 (Table 1), yellow glass. $^1$H-NMR ($^1$H 400 MHz, CDCl$_3$): δ=7.40-7.12 (m, 12 arom. H), 7.04-7.02 (m, 2 arom. H), 5.92 (s, C=CHH, 2H), 5.44 (s, C=CHH, 2H), 3.82-3.75 (m, OCH$_2$, 4H), 3.42 (d, J=13.2 Hz, CHH—C=CH$_2$, 2H), 3.33 (d, J=13.2 Hz, CHH—C=CH$_2$, 2H), 1.45-1.30 (m, CO$_2$CH$_2$CH$_2$, 4H), 1.29 (s, t-Bu), 1.23 (s, t-Bu), 1.15-1.08 (m, OCH$_2$CH$_2$CH$_2$,4H). $^{13}$C-NMR (100 MHz, CDCl$_3$): 178.5 (s); 166.8 (s); 149.2 (s); 147.0 (s); 139.3 (s); 136.3 (s); 133.4 (s); 129.2 (d); 128.4 (t); 128.3 (d); 128.2 (s); 127.4 (d); 123.3 (d); 121.7 (d); 64.9 (t); 56.6 (s); 39.6 (t); 35.2 (s); 34.6 (s); 32.0 (q); 29.9 (q); 28.7 (t); 25.9 (t).

EXAMPLE 8

Preparation of the Compound 108

Table 1

To a mixture of 10.0 g (28.5 mmol) of 5,7-di-tert-butyl-3-(2,3-dimethyl-phenyl)-3H-benzofuran-2-one and 5,7-di-tert-butyl-3-(3,4-dimethyl-phenyl)-3H-benzofuran-2-one [Irganox HP 136®; Ciba Specialty Chemicals Inc.] and 5.78 g (29.9 mmol) of 2-bromomethyl-acrylic acid ethyl ester in 100 ml of toluene is added at room temperature 1.76 g (31.4 mmol) of Brogli catalyst (50% aq. KOH/NaOH 10/1). The reaction mixture is heated under reflux for 2 hours, diluted with water (100 ml) and extracted with diethyl ether (150 ml). The organic phase is washed with brine (100 ml), dried over sodium sulfate and concentrated using a vacuum rotary evaporator. The crude material is purified by flash chromatography on silica gel with hexane/diethyl ether=10:1. The pure fractions give 11.65 g (88%) of compound 108 (Table 1) as a mixture of regioisomers (92.7% major isomer, 7.3% minor isomer), white solid, m.p. 106-111° C.

Major isomer: $^1$H-NMR ($^1$H 400 MHz, CDCl$_3$): δ=7.19-7.02 (m, 5 arom. H), 5.93 (s, C=CHH), 5.45 (s, C=CHH), 3.90-3.75 (m, OCH$_2$), 3.45 (d, J=13.6 Hz, CHH—C=CH$_2$), 3.30 (d, J=13.2 Hz, CHH—C=CH$_2$), 2.18 (s, Ph-CH$_3$), 2.16 (s, Ph-CH$_3$), 1.29 (s, t-Bu), 1.23 (s, t-Bu), 1.01 (t, J=7.0 Hz, OCH$_2$CH$_3$).

Minor isomer: $^1$H-NMR ($^1$H 400 MHz, CDCl$_3$) (significant peaks): δ=7.51-6.65 (m, 5 arom. H), 5.95 (s, C=CHH), 5.48 (s, C=CHH), 3.85-3.65 (m, OCH$_2$), 3.05 (d, J=12 Hz, CHH—C=CH$_2$), 2.14 (s, Ph-CH$_3$), 1.31 (s, t-Bu), 1.14 (s, t-Bu), 0.95-1.02 (m, OCH$_2$CH$_3$).

EXAMPLE 9

Preparation of the Compound 109

Table 1

To a suspension of 0.15 g (6.18 mmol) of sodium hydride in 5.0 ml of dry tetrahydrofuran (THF) is added dropwise at 0-5° C. 1.00 g (6.18 mmol) of diethyl malonate dissolved in 10 ml of dry THF. The mixture is stirred for 15 minutes at 0-5° C. then 1.19 g (6.18 mmol) of 2-bromomethyl-acrylic acid ethyl ester is added. The resulting mixture is stirred for 2 hours at 0-5° C., diluted with water and extracted with diethyl ether (50 ml). The organic phase is washed with 1M NH$_4$Cl (20 ml), dried over sodium sulfate and concentrated using a vacuum rotary evaporator. The crude material is purified by flash chromatography on silica gel with hexane/diethyl ether=4:1. The pure fractions give 1.22 g (73%) of compound 109 (Table 1), colourless liquid. $^1$H-NMR ($^1$H 400 MHz, CDCl$_3$): δ=6.22 (d, J=1.2 Hz, C=CHH), 5.65 (d, J=1.2 Hz, C=CHH), 4.25-4.10 (m, OCH$_2$, 6H), 3.71 (t, J=8.0 Hz, CO$_2$CHCO$_2$), 2.90 (t, J=8.0 Hz, CH$_2$—C=CH$_2$), 1.35-1.20 (m, OCH$_2$CH$_3$, 9H). $^{13}$C-NMR (100 MHz, CDCl$_3$): 169.1 (s); 166.6 (s); 137.1 (s); 128.0 (t); 61.8 (t); 61.3 (t); 51.2 (d); 31.8 (t); 14.5 (q); 14.4 (q); 14.2 (q). EI-MS: 272 (M$^+$).

EXAMPLE 10

Preparation of the Compound 110

Table 1

To a suspension of 0.45 g (18.6 mmol) of sodium hydride in 10 ml of dry tetrahydrofuran (THF) is added dropwise at 0-5° C. 2.00 g (16.9 mmol) of benzylcyanide dissolved in 15 ml of dry THF. The mixture is stirred for 15 minutes at 0-5° C. then 3.26 g (16.9 mmol) of 2-bromomethyl-acrylic acid ethyl ester is added. The resulting mixture is stirred for 3 hours at 0-5° C., diluted with water and extracted with diethyl ether (80 ml). The organic phase is washed with 1M NH$_4$Cl (30 ml), dried over sodium sulfate and concentrated using a vacuum rotary evaporator. The crude material is purified by flash chromatography on silica gel with hexane/diethyl ether=7:1. The pure fractions give 2.20 g (57%) of compound 110 (Table 1), colourless liquid. $^1$H-NMR ($^1$H 400 MHz, CDCl$_3$):

δ=7.45-7.30 (5 arom. H), 6.37 (s, C=CHH), 5.76 (s, C=CHH), 4.32-4.15 (m, OCH$_2$+CNCH), 2.97-2.75 (m, CH$_2$—C=CH$_2$), 1.34 (t, J=7.2 MHz, OCH$_2$CH$_3$).

EXAMPLE 11

Preparation of the Compound 111

Table 1

To a suspension of 0.12 g (5.00 mmol) of sodium hydride in 5.0 ml of dry tetrahydrofuran (THF) is added dropwise at 0-5° C. 1.00 g (5.00 mmol) of diphenylacetonitrile. The mixture is stirred for 20 minutes at 0-5° C. then 0.97 g (5.00 mmol) of 2-bromomethyl-acrylic acid ethyl ester is added. The resulting mixture is stirred for 3 hours at 0-5° C., diluted with water and extracted with diethyl ether (50 ml). The organic phase is washed with 1M NH$_4$Cl (20 ml), dried over sodium sulfate and concentrated using a vacuum rotary evaporator. The crude material is purified by flash chromatography on silica gel with hexane/diethyl ether=4:1. The pure fractions give 1.05 g (69%) of compound 111 (Table 1), colourless liquid. $^1$H-NMR ($^1$H 300 MHz, CDCl$_3$): δ=7.65-7.50 (m, 10 arom. H), 6.55 (s, C=CHH), 5.88 (s, C=CHH), 4.17 (q, J=7.2 Hz, OCH$_2$), 3.69 (s, CH$_2$—C=CH$_2$), 1.39 (t, J=7.2 Hz, OCH$_2$CH$_3$).

EXAMPLE 12

Preparation of the Compound 112

Table 1

To a suspension of 0.24 g (10.0 mmol) of sodium hydride in 5.0 ml of dry tetrahydrofuran (THF) is added dropwise at 0-5° C. 1.89 g (10.0 mmol) of ethyl phenylcyanoacetate. The mixture is stirred for 20 minutes at 0-5° C. then 1.93 g (10.0 mmol) of 2-bromomethyl-acrylic acid ethyl ester is added. The resulting mixture is stirred for 3 hours at 0-5° C., diluted with water and extracted with diethyl ether (50 ml). The organic phase is washed with 1M NH$_4$Cl (20 ml), dried over sodium sulfate and concentrated using a vacuum rotary evaporator. The crude material is purified by flash chromatography on silica gel with hexane/diethyl ether=2:1. The pure fractions give 2.28 g (76%) of compound 112 (Table 1), colourless liquid. $^1$H-NMR ($^1$H 300 MHz, CDCl$_3$): δ=7.72-7.62 (m, 2 arom. H), 7.62-7.40 (m, 3 arom. H), 6.50 (s, C=CHH), 5.85 (s, C=CHH), 4.50-4.32 (m, OCH$_2$), 4.32-4.18 (m, OCH$_2$), 3.56 (d, J=14.4 Hz, CHH—C=CH$_2$), 3.42 (d, J=14.4 Hz, CHH—C=CH$_2$), 1.45-1.30 (m, OCH$_2$CH$_3$, 6H).

EXAMPLE 13

Preparation of the Compound 113

Table 1

To a suspension of 0.16 g (6.69 mmol) of sodium hydride in 10 ml of dry tetrahydrofuran (THF) is added dropwise at 0-5° C. 1.50 g (6.69 mmol) of methyl fluorine-9-carboxylate dissolved in 10 ml of dry THF. The mixture is stirred for 30 minutes at 0-5° C. then 1.29 g (6.69 mmol) of 2-bromomethyl-acrylic acid ethyl ester is added. The resulting mixture is stirred for 1 hour at 0-5° C., diluted with water and extracted with diethyl ether (80 ml). The organic phase is washed with 1M NH$_4$Cl (30 ml), dried over sodium sulfate and concentrated using a vacuum rotary evaporator. The crude material is purified by recrystallization in hexane to give 1.62 g (78%) of compound 113 (Table 1), white solid, m.p. 68-70° C. $^1$H-NMR ($^1$H 400 MHz, CDCl$_3$): δ=7.60 (d, J=7.2 Hz, 2 arom. H), 7.50 (d, J=7.2 Hz, 2 arom. H), 7.32-7.12 (m, 4 arom. H), 5.63 (s, C=CHH), 4.81 (s, C=CHH), 3.80 (q, J=7.2 Hz, OCH$_2$), 3.54 (s, OCH$_3$), 3.34 (s, CH$_2$—C=CH$_2$), 1.00 (t, J=7.2 Hz, OCH$_2$CH$_3$). $^{13}$C-NMR (100 MHz, CDCl$_3$): 173.8 (s); 167.6 (s); 144.3 (s); 141.6 (s); 135.9 (s); 128.6 (d); 127.8 (t); 127.5 (d); 126.0 (d); 61.7 (t); 60.9 (s); 53.0 (q); 37.8 (t); 14.4 (q). EI-MS: 336 (M$^+$).

EXAMPLE 14

Preparation of the Compound 114

Table 1

To a mixture of 1.31 g (4.06 mmol) of 5,7-di-tert-butyl-3H-benzofuran-2-one and 1.57 g (8.12 mmol) of 2-bromomethyl-acrylic acid ethyl ester in 10 ml of toluene is added at room temperature 0.50 g (8.94 mmol) of Brogli catalyst (50% aq. KOH/NaOH 10/1). The reaction mixture is heated under reflux for 3 hours, diluted with water and extracted with diethyl ether (50 ml). The organic phase is washed with 1M NH$_4$Cl (30 ml), dried over sodium sulfate and concentrated using a vacuum rotary evaporator. The crude material is purified by flash chromatography on silica gel with hexane/diethyl ether=4:1. The pure fractions give 1.51 g (79%) of compound 114 (Table 1), pale yellow solid, m.p. 68-72° C. $^1$H-NMR ($^1$H 400 MHz, CDCl$_3$): δ=7.19 (d, J=2.0 Hz, 1 arom. H), 7.06 (d, J=2.0 Hz, 1 arom. H), 6.08 (s, C=CHH, 2H), 5.54 (s, C=CHH, 2H), 4.08-3.92 (m, OCH$_2$, 4H), 3.19 (d, J=13.2 Hz, CHH—C=CH$_2$, 2H), 2.95 (d, J=13.2 Hz, CHH—C=CH$_2$, 2H), 1.37 (s, t-butyl), 1.34 (s, t-butyl), 1.13 (t, J=7.2 Hz, OCH$_2$CH$_3$, 6H). $^{13}$C-NMR (100 MHz, CDCl$_3$): 179.1 (s); 167.1 (s); 149.2 (s); 146.7 (s); 136.5 (s); 133.2 (s); 128.7 (t); 127.1 (s); 123.2 (d); 121.3 (d); 61.2 (t); 53.9 (s); 39.0 (t); 35.3 (s); 34.7 (s); 32.2 (q); 30.1 (q); 14.7 (q). EI-MS: 470 (M$^+$).

EXAMPLE 15

Preparation of the Compound 115

Table 1

To a mixture of 1.29 g (4.00 mmol) of 5,7-di-tert-butyl-3-phenyl-3H-benzofuran-2-one and 0.73 g (4.00 mmol) of 2-benzenesulfinyl-prop-2-en-1-ol in 4.0 ml of toluene is added at room temperature 0.10 g (1.6 mmol) of Brogli catalyst (50% aq. KOH/NaOH 10/1). The reaction mixture is heated under reflux for 6 hours, diluted with water and extracted with diethyl ether (50 ml). The organic phase is washed with 1M NH$_4$Cl (30 ml), dried over sodium sulfate and concentrated using a vacuum rotary evaporator. The crude material is purified by flash chromatography on silica gel with hexane/diethyl ether=2:1. The pure fractions give 0.77 g (40%) of compound 115 (Table 1) as a mixture of diastereoisomers. Isomer 1: white solid, m.p. 63-69° C. Isomer 2: colourless liquid.

Isomer 1: $^1$H-NMR ($^1$H 400 MHz, CDCl$_3$): δ=7.65-7.58 (m, 2 arom. H), 7.52-7.45 (m, 3 arom. H), 7.40-7.25 (m, 6 arom. H), 7.21 (d, J=2.0 Hz, 1 arom. H), 5.88 (s, C=CHH), 5.20 (s, C=CHH), 3.18 (d, J=15.2 Hz, CHH—C=CH$_2$), 2.95 (d, J=15.2 Hz, CHH—C=CH$_2$), 1.44 (s, t-butyl), 1.37 (s, t-butyl).

Isomer 2: $^1$H-NMR ($^1$H 400 MHz, CDCl$_3$): δ=7.50-7.35 (m, 5 arom. H), 7.32-7.20 (m, 6 arom. H), 7.05 (d, J=2.0 Hz, 1 arom. H), 6.07 (s, C=CHH), 5.79 (s, C=CHH), 3.27 (d, J=15.2 Hz, CHH—C=CH$_2$), 2.42 (d, J=15.2 Hz, CHH—C=CH$_2$), 1.34 (s, t-butyl), 1.33 (s, t-butyl).

EXAMPLE 16

Preparation of the Compound 116

Table 1

To a suspension of 0.12 g (5.00 mmol) of sodium hydride in 5.0 ml of dry tetrahydrofuran (THF) is added dropwise at 0-5° C. 0.89 g (4.00 mmol) of 2-phenyl-1,3-indandione dissolved in 5.0 ml of dry THF. The mixture is stirred for 30 minutes at 0-5° C. then 1.23 g (5.00 mmol) of (3-bromo-prop-1-ene-2-sulfinyl)-benzene is added. The resulting mixture is stirred for 3 hours at 0-5° C., diluted with water and extracted with diethyl ether (50 ml). The organic phase is washed with 1M NH$_4$Cl (20 ml), dried over sodium sulfate and concentrated using a vacuum rotary evaporator. The crude material is purified by flash chromatography on silica gel with hexane/diethyl ether=1:4. The pure fractions give 0.46 g (30%) of compound 116 (Table 1), white solid, m.p. 118-120° C. $^1$H-NMR ($^1$H 400 MHz, CDCl$_3$): δ=8.15-8.00 (m, 2 arom. H), 8.00-7.85 (m, 2 arom. H), 7.80-7.70 (m, 2 arom. H), 7.62-7.50 (m, 3 arom. H), 7.45-7.20 (m, 5 arom. H), 6.10 (s, C=CHH), 5.68 (s, C=CHH), 3.18 (d, J=15.2 Hz, CHH—C=CH$_2$), 2.70 (d, J=15.2 Hz, CHH—C=CH$_2$). EI-MS: 387 (M$^+$).

EXAMPLE 17

Preparation of the Compound 117

Table 1

To a suspension of 84 mg (3.50 mmol) of sodium hydride in 5.0 ml of dry tetrahydrofuran (THF) is added dropwise at 0-5° C. 0.68 g (3.50 mmol) of diphenylacetonitrile in 1.0 ml of dry THF. The mixture is stirred for 30 minutes at 0-5° C. then 0.86 g (3.50 mmol) of (3-bromo-prop-1-ene-2-sulfinyl)-benzene is added. The resulting mixture is stirred for 3 hours at 0-5° C., diluted with water and extracted with diethyl ether (40 ml). The organic phase is washed with 1M NH$_4$Cl (10 ml), dried over sodium sulfate and concentrated using a vacuum rotary evaporator. The crude material is purified by flash chromatography on silica gel with hexane/diethyl ether=1:4. The pure fractions give 0.70 g (56%) of compound 117 (Table 1), white solid, m.p. 114-118° C. $^1$H-NMR ($^1$H 400 MHz, CDCl$_3$): δ=7.60-7.45 (m, 5 arom. H), 7.40-7.15 (m, 10 arom. H), 6.23 (s, C=CHH), 5.81 (s, C=CHH), 3.38 (d, J=16.0 Hz, CHH—C=CH$_2$), 2.72 (d, J=16.0 Hz, CHH—C=CH$_2$). EI-MS: 357 (M$^+$).

EXAMPLE 18

Preparation of the Compound 118

Table 1

To a suspension of 0.12 g (5.00 mmol) of sodium hydride in 5.0 ml of dry tetrahydrofuran (THF) is added dropwise at 0-5° C. 0.76 g (5.00 mmol) of ethyl phenylcyanoacetate. The mixture is stirred for 30 minutes at 0-5° C. then 1.23 g (5.00 mmol) of (3-bromo-prop-1-ene-2-sulfinyl)-benzene is added. The resulting mixture is stirred for 1 hour at room temperature, diluted with water and extracted with diethyl ether (50 ml). The organic phase is washed with 1M NH$_4$Cl (20 ml), dried over sodium sulfate and concentrated using a vacuum rotary evaporator. The crude material is purified by flash chromatography on silica gel with hexane/diethyl ether=1:4. The pure fractions give 1.27 g (90%) of compound 118 (Table 1) as a mixture of diastereoisomers, yellow liquid. $^1$H-NMR ($^1$H 300 MHz, CDCl$_3$): δ=7.52-7.10 (m, 10 arom. H), 6.11 (s, C=CHH, isomer 1), 6.07 (s, C=CHH, isomer 2), 5.75 (s, C=CHH, isomer 1), 5.60 (s, C=CHH, isomer 2), 4.15-3.90 (m, OCH$_2$), 3.03 (d, J=16.2 Hz, CHH—C=CH$_2$, isomer 1), 2.84 (d, J=16.2 Hz, CHH—C=CH$_2$, isomer 2), 2.61 (d, J=16.2 Hz, CHH—C=CH$_2$, isomer 2), 2.41 (d, J=16.2 Hz, CHH—C=CH$_2$, isomer 1), 1.10-0.95 (m, OCH$_2$CH$_3$).

EXAMPLE 19

Preparation of the Compound 119

Table 1

To a suspension of 0.19 g (8.00 mmol) of sodium hydride in 5.0 ml of dry tetrahydrofuran (THF) is added dropwise at 0-5° C. 1.12 g (5.00 mmol) of methyl fluorene-9-carboxylate dissolved in 5.0 ml of dry THF. The mixture is stirred for 30 minutes at 0-5° C. then 1.96 g (8.00 mmol) of (3-bromo-prop-1-ene-2-sulfinyl)-benzene is added. The resulting mixture is stirred for 1 hour at room temperature, diluted with water and extracted with diethyl ether (50 ml). The organic phase is washed with 1M NH$_4$Cl (20 ml), dried over sodium sulfate and concentrated using a vacuum rotary evaporator. The crude material is purified by flash chromatography on silica gel with hexane/diethyl ether=1:2. The pure fractions give 1.23 g (63%) of compound 119 (Table 1) as a mixture of diastereoisomers, yellow solid, m.p. 122-124° C. $^1$H-NMR ($^1$H 300 MHz, CDCl$_3$): δ=7.80-7.74 (m, 2 arom. H), 7.55-7.30 (m, 11 arom. H), 5.74 (s, C=CHH), 4.88 (s, C=CHH), 3.58 (s, OCH$_3$), 3.28 (d, J=15.3 Hz, CHH—C=CH$_2$), 2.85 (d, J=15.3 Hz, CHH—C=CH$_2$).

EXAMPLE 20

Preparation of the Compound 120

Table 1

To a mixture of 3.22 g (10.0 mmol) of 5,7-di-tert-butyl-3-phenyl-3H-benzofuran-2-one and 0.83 g (10.0 mmol) of 2-hydroxymethyl-acrylonitrile in 10 ml of toluene is added at room temperature 0.11 g (2.00 mmol) of Brogli catalyst (50% aq. KOH/NaOH 10/1). The reaction mixture is heated under reflux for 5 hours, diluted with water (20 ml) and extracted with diethyl ether (50 ml). The organic phase is washed with 1M NH$_4$Cl (20 ml), brine (20 ml), dried over sodium sulfate and concentrated using a vacuum rotary evaporator. The crude material is purified by flash chromatography on silica gel with hexane/diethyl ether=4:1. The pure fractions give 2.47 g (64%) of compound 120 (Table 1), pale yellow liquid. $^1$H-NMR ($^1$H 300 MHz, CDCl$_3$): δ=7.40-7.12 (m, 7 arom. H), 5.81 (s, C=CHH), 5.72 (s, C=CHH), 3.32 (d, J=13.5 Hz, CHH—C=CH$_2$), 3.06 (d, J=16.2 Hz, CHH—C=CH$_2$), 1.34 (s, t-butyl), 1.29 (s, t-butyl).

EXAMPLE 21

Preparation of the Compound 121

Table 1

To a mixture of 5.80 g (30.0 mmol) of diphenylacetonitrile and 2.74 g (33.0 mmol) of 2-hydroxymethyl-acrylonitrile in 30 ml of toluene is added at room temperature 0.34 g (6.00 mmol) of Brogli catalyst (50% aq. KOH/NaOH 10/1). The reaction mixture is heated under reflux for 5 hours, diluted with water (60 ml) and extracted with diethyl ether (150 ml). The organic phase is washed with 1M NH$_4$Cl (60 ml), brine (60 ml), dried over sodium sulfate and concentrated using a vacuum rotary evaporator. The crude material is purified by flash chromatography on silica gel with hexane/ethyl acetate=2:1. The pure fractions give 2.06 g (27%) of compound 121 (Table 1), pale yellow liquid. $^1$H-NMR ($^1$H 400 MHz, CDCl$_3$): δ=7.42-7.2 (m, 10 arom. H), 6.02 (s, C=CHH), 5.89 (s, C=CHH), 3.24 (s, CHH—C=CH$_2$), 3.06 (d, J=16.2 Hz, CHH—C=CH$_2$), 1.34 (s, tert-butyl), 1.29 (s, tert-butyl).

TABLE 1

(101)
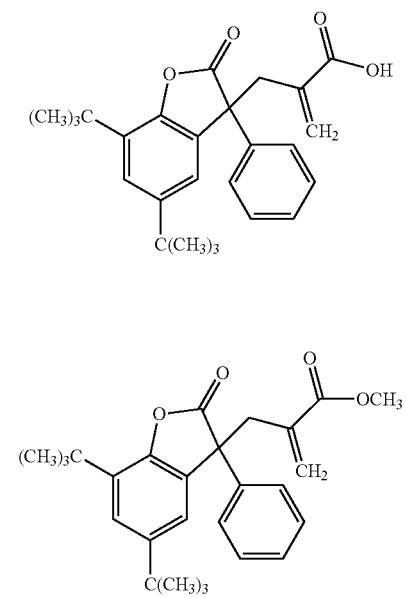

(102)
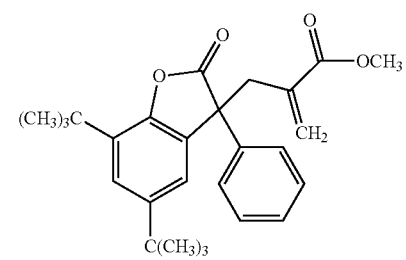

(103)
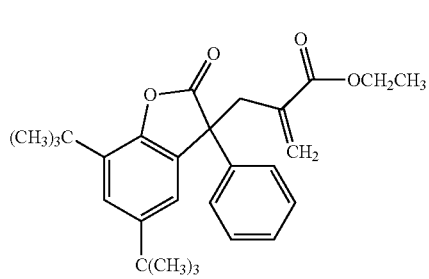

(104)
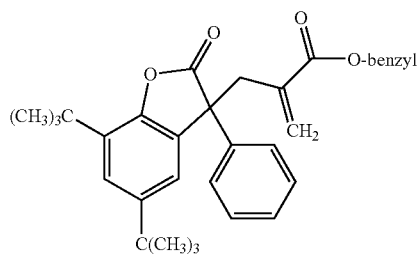

(105)
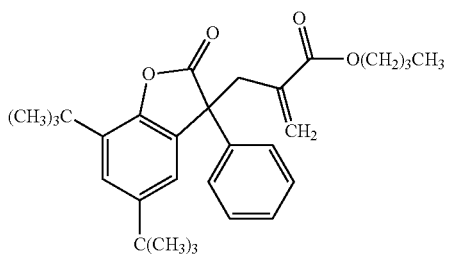

(106)
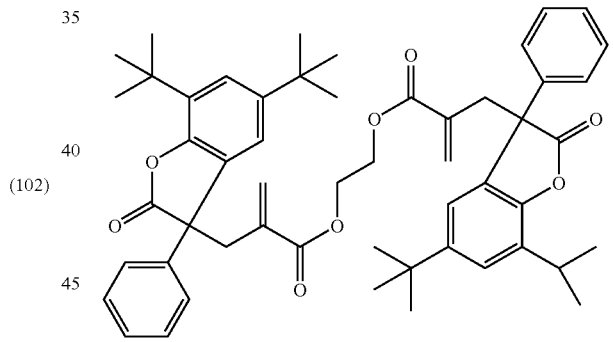

(107)
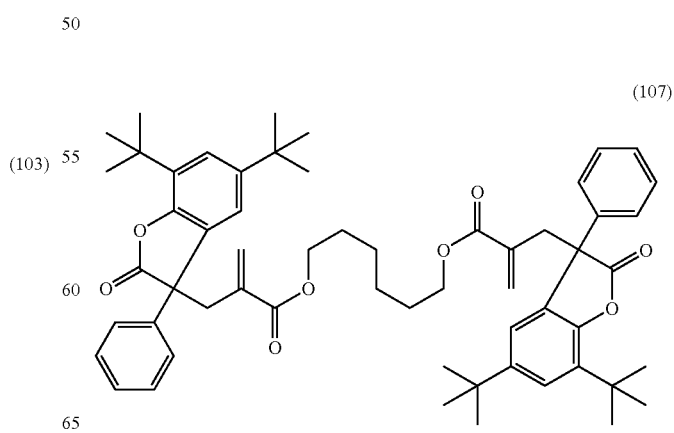

TABLE 1-continued
(108)
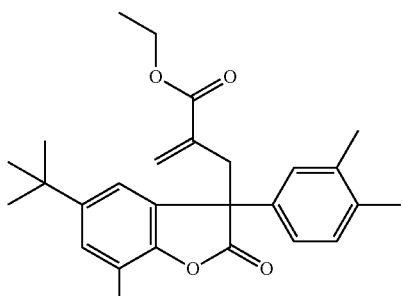
(109)
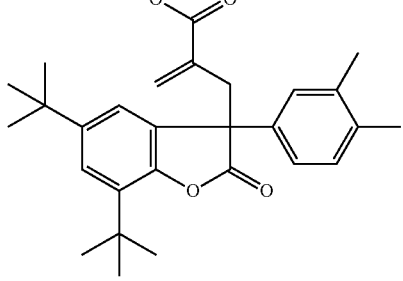
(110)
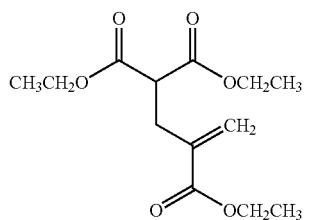
(111)
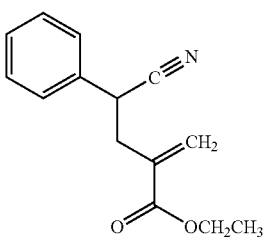
TABLE 1-continued
(112)
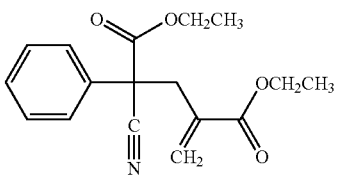
(113)
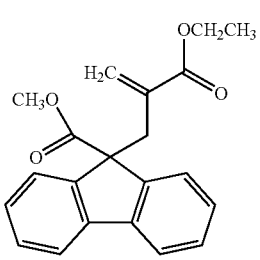
(114)
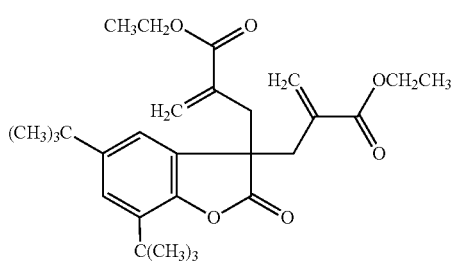
(115)
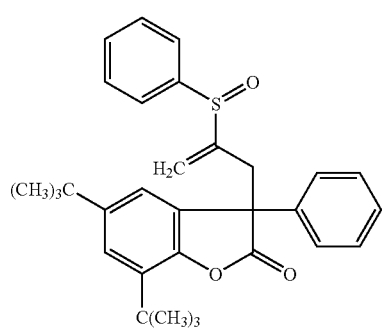
(116)
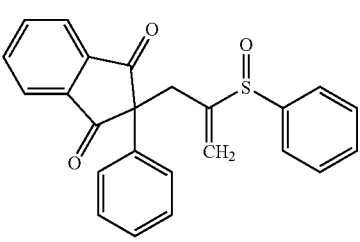
(117)
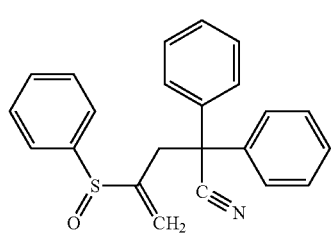

TABLE 1-continued (118) 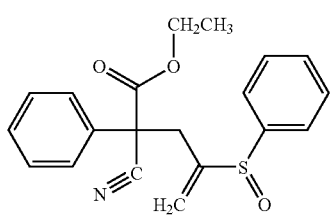

(119) 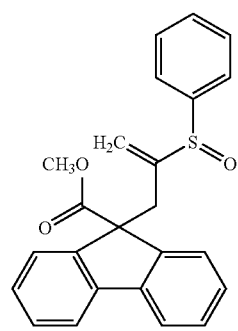

(120) 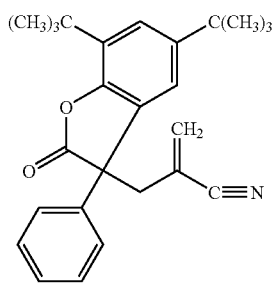

(121) 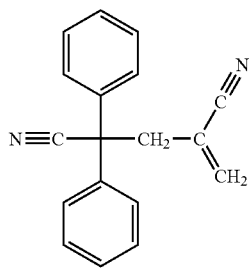

EXAMPLE 22

Stabilization of Multiple-Extruded Polypropylene 1.3 kg of polypropylene powder (Profax 6501), which has been prestabilized with 0.025% of Irganox®1076 (n-octadecyl 3-[3,5-di-tert-butyl-4-hydroxyphenyl]propionate) (melt index 3.2 g/10 min, measured at 230° C./2.16 kg) are blended with 0.05% of Irganox®1010 (pentaerythritol tetrakis[3-(3, 5-di-tert-butyl-4-hydroxyphenyl)propionate]), 0.05% of calcium stearate, 0.03% of DHT 4A® (Kyowa Chemical Industry Co., Ltd., [$Mg_{4.5}Al_2(OH)_{13}CO_3 \cdot 3.5H_2O$]) and 0.015% of compound of Table 1. This blend is then extruded in an extruder having a cylinder diameter of 20 mm and a length of 400 mm at 100 rpm, the 3 heating zones being adjusted to the following temperatures: 260, 270, 280° C. The extrudate is cooled by drawing it through a water bath and is then granulated. This granulate is repeatedly extruded. After 3 extrusions, the melt index is measured (at 230° C./2.16 kg). A substantial increase in the melt index denotes pronounced chain degradation, i.e. poor stabilization. The results are summarized in Table 2.

TABLE 2

| Compound of Table 1 | Melt index after 3 extrusions |
|---|---|
| — | 17.8 |
| 101 | 5.2 |
| 103 | 5.3 |
| 108 | 5.1 |
| 114 | 5.2 |
| 115 | 5.1 |

EXAMPLE 23

Stabilization of Polyethylene During Processing 100 parts of polyethylene powder (Lupolen®5260 Z) are blended with 0.05 part of Irganox®1010 (pentaerythritol tetrakis[3-(3,5-di-tert-butyl-4-hydroxyphenyl)propionate]) and 0.05 part of a compound of Table 1 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 3 as a measure of the stabilizing action. The longer this time is the better the stabilizing action.

TABLE 3

| Compound of Table 1 | Time until increase in torque (min) |
|---|---|
| — | 10.3 |
| 102 | 28.0 |
| 104 | 28.1 |
| 107 | 27.9 |
| 114 | 27.9 |
| 120 | 28.2 |

EXAMPLE 24

Stabilization of Multiple-Extruded Polypropylene at High Temperature 1.5 kg of polypropylene powder (Profax 6501), which has been prestabilized with 0.008% of Irganox®1076 (n-octadecyl 3-[3,5-di-tert-butyl-4-hydroxyphenyl]propionate) (melt index 3.2 g/10 min, measured at 230° C./2.16 kg) are blended with 0.05% of Irganox®1010 (pentaerythritol terakis[3-(3,5-di-tert-butyl-4-hydroxyphenyl)propionate]), 0.10% of calcium stearate and 0.015 to 0.100% of stabilizer or stabilizer mixture according to Table 4. This blend is then extruded in an extruder having a cylinder diameter of 20 mm and a length of 400 mm at 100 rpm, the 3 heating zones being adjusted to the following temperatures: 280, 320, 340° C. The extrudate is cooled by drawing it through a water bath and is then granulated. This granulate is repeatedly extruded. After 5 extrusions, the melt index is measured (at 230° C./2.16 kg). A substantial increase in the melt index denotes pronounced chain degradation, i.e. poor stabilization. The results are summarized in Table 4.

TABLE 4

| Stabilizers | Concentration in % (by weight) | Melt index after 5 extrusions | | |
|---|---|---|---|---|
| | | 280° C. | 320° C. | 340° C. |
| Irgafos ® 168[a)] | 0.100 | 9.8 | 43.8 | 80.3 |
| Sandostab ® P-EPQ[b)] | 0.050 | 6.5 | 24.1 | 62.1 |
| Compound 108 | 0.015 | 8.4 | 19.4 | 22.6 |
| Irgafos ® 168[a)] | 0.045 | 7.3 | 19.3 | 26.6 |
| Compound 108 | 0.005 | | | |
| Sandostab ® P-EPQ[b)] | 0.045 | 5.9 | 16.9 | 25.6 |
| Compound 108 | 0.005 | | | |

For footnotes a) and b) see the end of Table 23.

EXAMPLE 25

Preparation of Polyether/Polyurethane Soft Foams as Well as the Stabilization Thereof Exactly 470 mg (0.3%, based on the polyol) of a stabilizer of this invention is dissolved in 157 g of an antioxidant-free polyether/polyol, Lupranol®2045 (trifunctional polyether/polyol having primary hydroxyl groups; hydroxyl number 35 mg KOH/g, water content less than 0.1%, acid number less than 0.1 mg KOH/g). 10.24 g of a solution consisting of 1.74 g Tecostab® (polysilicone supplied by Goldschmidt, Germany], 0.48 g diazabicyclooctane (amine catalyst) and 0.8 g of water are added and the reaction mixture is stirred vigorously for 60 seconds at 100 rpm. 3.2 g of a solution of 0.32 g of tin octoate (catalyst) in 2.9 g of the above polyol is added and the reaction mixture is again stirred vigorously for 60 seconds at 100 rpm. With vigorous stirring, 98 g of an isocyanate (Lupranat®T80, supplied by BASF; toluoylene-2,4- and toluoylene-2,6-diisocyanate mixture) are then added immediately and after 6 seconds the mixture is poured into a lined mould and the exothermic temperature is measured during foaming to a foam block. The foam blocks are cooled for 24 hours in a climatic chamber at 5° C. and stored. 2 cm slices are sawed from the center of the blocks and round (cylindrical) test samples are cut therefrom using a boring tool. The samples are aged in a test tube in the presence of air at room temperature and 200° C. for 30 minutes in a preheated alu-block thermostat (dynamic heat test). The yellowing of these test samples is determined as Yellowness Index (YI) according to ASTM D-1925-77. Low YI values denote little discoloration, high YI values severe discoloration of the samples. The results are summarized in Tables 5 and 6.

TABLE 5

| Example | Concentration of stabilizers in % (by weight) | YI room temp. | YI 200° C. |
|---|---|---|---|
| 25a[i)] | — | 1.1 | 69.2 |
| 25b[k)] | 0.15% Compound 103 0.15% Irganox ® 5057[c)] | −1.0 | 1.9 |
| 25c[k)] | 0.15% Compound 106 0.15% Irganox ® 5057[c)] | −1.0 | 1.9 |
| 25d[k)] | 0.15% Compound 108 0.15% Irganox ® 5057[c)] | −1.1 | 1.8 |

TABLE 6

| Example | Concentration of stabilizers in % (by weight) | YI room temp. | YI 200° C. |
|---|---|---|---|
| 25e[i)] | — | 1.0 | 69.3 |
| 25f[k)] | 0.10% Compound 103 0.10% Irganox ® 5057[c)] 0.10% Irganox ® 1135[d)] | −1.1 | 2.0 |
| 25g[k)] | 0.10% Compound 106 0.10% Irganox ® 5057[c)] 0.10% Irganox ® 1135[d)] | −1.0 | 1.9 |
| 25h[k)] | 0.10% Compound 108 0.10% Irganox ® 5057[c)] 0.10% Irganox ® 1135[d)] | −1.1 | 2.0 |

For footnotes c), d), i) and k) see the end of Table 23.

EXAMPLE 26

Stabilizing Polypropylene Fibers Processed at 300° C.

2.0 kg of polypropylene powder (B 10 FB® from Polychim S.A., France), which has a melt index of 12.0 g/dmin measured in accordance with DIN 53735 at 230° C. under 2.16 kg, is homogenized with 0.05% of calcium stearate and with the stabilizers indicated in Tables 7 and 8 for 2 minutes in a high-speed mixer. This mixture is extruded at 60 revolutions per minute in an extruder having a barrel diameter of 20 mm and a length of 400 mm, the three heating zones being set at the following temperatures: 200, 220 and 220° C. The extrudate is passed through a water bath for cooling and then granulated. These granules are processed to give a multifilament fiber. This is done using a single-screw extruder with a melt pump and a 37-hole spinning head. The maximum processing temperature is 300° C.

A portion of the unstretched fiber thus obtained is pressed for 6 minutes at 230° C. to form a sheet with a thickness of 2 mm. The melt index (MFI, melt flow index) of this sheet is measured in accordance with DIN 53735 at 230° C. and 2.16 kg. A large increase in the melt index denotes severe chain degradation and thus poor stabilization. The results are compiled in Table 7.

Another portion of the unstretched fiber thus obtained is treated with a lubricant (Limanol®P 25, Schill und Seilacher, Böblingen, Germany) and subjected to preliminary drawing. This preliminary drawing leads to a fiber strand having a linear density of 416 g/90 m. This means that a fiber strand 90 m in length has a weight of 416 g. In a further operation, this fiber strand is again drawn at 120° C. by a factor of 3.2 using a drawing apparatus. This leads to a fiber strand having a linear density of 130 g/90 m.

A portion of this fiber strand is used to produce a knitted tube. The yellowness index ($YI_1$) of this knitted tube is determined in accordance with ASTM D 1925-77. Low $YI_1$ values denote little discoloration, high $YI_1$ values severe discoloration of the samples. The results are compiled in Table 7. This knitted tube is exposed in the presence of from 4 to 6 ppm nitrogen dioxide ($NO_2$) at 40° C. and 87% relative atmospheric humidity for 48 hours in accordance with AATCC 164. The yellowness index ($YI_2$) of this exposed knitted tube is determined in accordance with ASTM D 1925-77. Low $YI_2$ values denote little discoloration, high $YI_2$ values severe discoloration of the samples. The results are compiled in Table 7.

Another portion of the fiber strand is used to carry out an oven ageing test at 100° C. In this test, a measurement is made, in days, of the time taken for the fiber strand to tear under the test conditions. The longer the period before tearing of the fiber strand, the better the stabilization. The results are compiled in Table 8.

Another portion of the unstretched fiber is pressed for 6 minutes at 230° C. to form a thin film with a thickness of 0.10 mm. This film is subjected to a Xenon test in accordance with DIN 53387. In this test, the film is exposed in a Xenon 1200 weathering apparatus until a carbonyl index of 0.25 is observed in the wavelength range from 1760 to 1680 cm$^{-1}$. The larger the number, the better the stabilization. The results are compiled in Table 8.

TABLE 7

| Example | Stabilizers | YI$_1$ after spinning | YI$_2$ after NO$_2$ exposure | MFI after spinning |
|---|---|---|---|---|
| 26a[i] | — | 0.3 | 1.3 | 108.0 |
| 26b[k] | 0.100% Compound 108<br>0.050% Tinuvin ® 622[e] | 1.4 | 4.4 | 33.4 |
| 26c[k] | 0.100% Compound 108<br>0.050% Chimassorb ® 944[f] | 1.5 | 4.3 | 32.9 |
| 26d[k] | 0.100% Compound 108<br>0.050% Chimassorb ® 119[g] | 1.4 | 4.2 | 32.3 |
| 26e[k] | 0.075% Compound 108<br>0.050% Tinuvin ® 622[e]<br>0.075% Irgafos ® 168[a] | 0.8 | 4.3 | 32.4 |
| 26f[k] | 0.075% Compound 108<br>0.050% Chimassorb ® 944[f]<br>0.075% Irgafos ® 168[a] | 1.4 | 4.4 | 33.1 |
| 26g[k] | 0.075% Compound 108<br>0.050% Chimassorb ® 944[f]<br>0.075% Irgafos ® 38[h] | 1.5 | 4.5 | 32.6 |
| 26h[k] | 0.075% Compound 108<br>0.050% Chimassorb ® 119[g]<br>0.075% Irgafos ® 168[a] | 1.4 | 4.4 | 32.4 |

For footnotes a), e), f), g), h), i) and k) see the end of Table 23.

TABLE 8

| Example | Stabilizers | Oven ageing (days) | Xenon test (hours) |
|---|---|---|---|
| 26a[i] | — | 1 | 198 |
| 26c[k] | 0.100% Compound 108<br>0.050% Chimassorb ® 944[f] | 39 | 1350 |
| 26d[k] | 0.100% Compound 108<br>0.050% Chimassorb ® 119[g] | 38 | 1420 |
| 26f[k] | 0.075% Compound 108<br>0.050% Chimassorb ® 944[f]<br>0.075% Irgafos ® 168[a] | 39 | 1360 |
| 26g[k] | 0.075% Compound 108<br>0.050% Chimassorb ® 944[f]<br>0.075% Irgafos ® 38[h] | 38 | 1365 |
| 26h[k] | 0.075% Compound 108<br>0.050% Chimassorb ® 119[g]<br>0.075% Irgafos ® 168[a] | 39 | 1590 |

For footnotes a), f), g), h), i) and k) see the end of Table 23.

EXAMPLE 27

Preparation of Polyolefin Hollow Articles by the Rotomolding Process

100 Parts of low density polyethylene, copolymerized with hexene (PE-LLD), type Quantum® Petrothene® GA-635-661, having a melt flow index of 6.5 g/10 min and a density of 0.935 g/cm$^3$, are mixed with 0.170 part of Chimassorb® 944 [formula see footnote f) after Table 23], 0.050 part of zinc stearate and the stabilizers cited in Tables 9 and 10 at 232° C. in a Superior/MPM Extruder, fitted with a 24:1 Maddock type L/D screw, at 100 revolutions per minute. The polymer is then ground. The particle size of the polymer is from 150 to 500 µm. Owing to the larger surface of the particles obtained by grinding, the heat can be absorbed faster, which goes hand in hand with a lower energy consumption.

The actual rotomolding process or rotational molding process, which permits the production of fairly large three-dimensional solids, is carried out in a Clamshell type rotomolder FSP M20. In this machine, an aluminium mold, which is mounted on an arm and into which the plastic sample is filled, is heated with a gas burner with circulation of the hot air over 5 minutes to 316° C., or over 6 minutes to 329° C., and is then kept at this temperature for a specific time (see Tables 9 and 10). Subsequently, the oven is opened and the mold is cooled first for 7 minutes with circulating air, then for 7 minutes by spraying with water and finally for another 2 minutes with circulating air. During the entire heating and cooling process, the mold, which is mounted on two axes at right angles to each other, is rotated, the speed of the main axis being kept at 6 revolutions per minute and the rotational ratio being 4.5:1. After cooling, the lid of the mold is opened and the resultant hollow article is taken out. The yellowness index (YI) of the exterior of the molded articles is determined according to ASTM D 1925-70. Low YI values denote little discoloration, high YI values strong discoloration of the samples. The less discoloration, the more effective the stabilizer. The results are summarized in Tables 9 and 10.

TABLE 9

Rotomolding at 316° C.

| | | Yellowness Index after | |
|---|---|---|---|
| Examples | Stabilizer | 8 minutes | 10 minutes |
| Example 27a[i] | 0.05% Irganox ® 1010[b]<br>0.10% Irgafos ® 168[a] | 6.4 | 18.0 |
| Example 27b[k] | 0.02% compound 107<br>0.08% Irgafos ® 168[a] | 4.8 | 5.6 |

TABLE 10

Rotomolding at 329° C.

| | | Yellowness Index after | |
|---|---|---|---|
| Examples | Stabilizer | 6 minutes | 8 minutes |
| Example 27c[i] | 0.05% Irganox ® 1010[b]<br>0.10% Irgafos ® 168[a] | 4.0 | 16.7 |
| Example 27d[k] | 0.02% compound 107<br>0.08% Irgafos ® 168[a] | 4.0 | 6.1 |

For footnotes a), i), k) and l) see the end of Table 23.

EXAMPLE 28

Stabilisation of Polyethylene which is in Permanent Contact with Water 0.10% by weight of calcium stearate and a stabilizer mixture comprising 0.10% by weight of Irganox®1010 (pentaerythritol tetrakis[3-(3,5-di-tert-butyl-4-hydroxyphenyl) propionate]), 0.05% by weight of Irgafos®168 (tris(2,4-di-tert-butylphenyl)phosphite) and 0.05% by weight of compound 106 (Table 1) is added dry to a polyethylene polymer (Hostalene® CRP 100; PE-HD) taken direct from a reactor and are incorporated therein in a Pappenmaier mixer (type 20) within 2 minutes.

In an extruder, of Schwabenthan, the stabilized polyethylene is homogenised and processed to granulate. For the extraction tests in water, 200 mm by 150 mm by 2 mm test plates are pressed from the granulate of the individual formulations using a table press. To ease the demoulding of the test plates, the pressing process is carried out between two aluminium foils.

The stabilizer extraction tests are carried out with deionised water. Preliminary heating of the extraction vessels is carried out in a circulating air oven, of Heraeus (Hanau, Germany), at a maximum temperature deviation of 1.5° C. Glass vessels are used for extraction tests below the boiling point of water, such as at 80° C. Owing to the risk of oversaturating the water with stabilizers, the amount of liquid used for the tests is fixed at c. 400 ml per c. 70 g of polymer and the water is replaced with fresh water at regular intervals, i.e. whenever a sample is taken.

The test plates are subjected to the above test conditions for 50 days at 80° C. Upon termination of the extraction test, the residual stabilizer content and the oxidation induction time of the test plates are determined.

The residual content of sterically hindered phenol, Irganox®1010, is determined using an internal standard in an HPLC appliance of the Spectra Physics SP 8800 type, equipped with autosampler and UV/VIS detector of the Spectra 200 type. The chromatography is carried out at room temperature using a Hyperchrome 125×4.6 mm type column which is filled with Nucleosil C 185 µm. The injection volume is 14 µl at a flow rate of 1.5 ml/minute. UV detection takes place at 270 nm.

The oxidation induction time which is determined using a "DuPont-instrument 910 Differential Scanning Calorimeter", of TA Instruments (Alzenau, Germany), and taking a 5 to 10 mg amount of sample, describes the time in minutes at constant thermal stress (190° C./$O_2$) up to the start of the complete degradation of the polyethylene sample. The longer the oxidation induction time, the better stabilized the polyethylene and the more stable is the polyethylene against extracting water with which it is in permanent contact. The results show that the stability of polyolefins which are in permanent contact with extracting media is improved if they contain a compound of the formula I according to the instant invention as stabilizer.

EXAMPLE 29

Measuring the Discoloration of Powder Coatings Based on a Carboxy-Functional Polyester and Cured in Electric and Gas Ovens To prepare the powder coating composition based on a carboxy-functional polyester, components 1 to 6 (formulation without additives) or components 1 to 7 (formulation containing the stabilizers) are employed in the sequence indicated (cf. Table 11).

TABLE 11

| Components | Examples (amount in grams) | |
|---|---|---|
| | 29a | 29b to 29i |
| 1. Crylcoat ® 360[a] | 591 | 591 |
| 2. Araldit ® GT 7004[b] | 394 | 394 |
| 3. Octadecyltrimethylammonium bromide[c] | 3.6 | 3.6 |
| 4. Resiflow ® PV 88[d] | 12 | 12 |
| 5. Benzoin[e] | 3 | 3 |
| 6. Titanium dioxide type R-KB-5[f] | 500 | 500 |
| 7. Stabilizers (see Tables 12 and 13) | — | 6 |
| Total: | 1503.6 | 1509.6 |

[a]Crylcoat ® 360 from UCB S.A., Drogenbos, Belgium.
[b]Araldit ® GT 7004 (Ciba Specialty Chemicals Inc.) is a bisphenol A diglycidyl ether.
[c]Octadecyltrimethylammonium bromide from Fluka AG, Buchs, Switzerland.
[d]Resiflow ® PV 88 from Worlee Chemie GmbH, Lauenburg, Germany.
[e]Benzoin from Fluka AG.
[f]Titanium dioxide type R-KB-5 from Bayer AG, Leverkusen, Germany.

The components weighed out in this way are mixed using a planetary stirrer. The mixture is then extruded on a prism extruder at 300 revolutions/minute and at 100° C. and is rolled out. The powder coating composition is coarsely comminuted using a bench cutter and is ground in a Retsch ZM-1 ultracentrifugal mill with a 0.75 mm annular-perforation screen at 15,000 revolutions/minute. Finally, the powder is passed through a 30 µm screen on a centrifugal screening machine.

The finished powder coating composition is sprayed electrostatically to a coat thickness of 70 µm onto aluminium panels using an ESB-Wagner corona cup gun at 60 kV. Some of the coated panels are cured at 180° C. for 90 minutes in an electric oven. The remaining coated panels are cured at 180° C. for 45 minutes in a gas oven with an $NO_2$ content of 20 ppm. The yellowness index (YI) of the samples is determined in accordance with ASTM D 1925-70. Low YI values denote little discoloration, high YI values denote severe discoloration of the samples. The less the discoloration, the more effective the stabilizer. The results are summarized in Tables 12 and 13.

TABLE 12

| Curing for 90 minutes in an electric oven at 180° C. | | |
|---|---|---|
| Examples | Stabilizers (% rel. to components 1 to 5) | Yellowness index after 90 minutes (ASTM D 1925-70) |
| Example 29a[i] | — | 3.0 |
| Example 29b[k] | 0.60% Compound 118 | 2.6 |
| Example 29c[k] | 0.50% Irgafos ® 168[a] 0.10% Compound 118 | 2.6 |
| Example 29d[k] | 0.15% Irgafos ® 168[a] 0.15% HALS mixture[m] 0.30% Compound 118 | 2.5 |
| Example 29e[k] | 0.15% Irgafos ® 168[a] 0.15% Irganox ® 1010[l] 0.30% Compound 118 | 2.6 |

For footnotes a), i), k), m) and l) see the end of Table 23.

TABLE 13

| Curing for 45 minutes in a gas oven at 180° C. | | |
|---|---|---|
| Examples | Stabilizers (% rel. to components 1 to 5) | Yellowness index after 90 minutes (ASTM D 1925-70) |
| Example 29f[i] | — | 4.3 |
| Example 29g[k] | 0.60% Compound 118 | 3.3 |
| Example 29h[k] | 0.50% Irgafos ® 168[a] 0.10% Compound 118 | 3.2 |

TABLE 13-continued

Curing for 45 minutes in a gas oven at 180° C.

| Examples | Stabilizers (% rel. to components 1 to 5) | Yellowness index after 90 minutes (ASTM D 1925-70) |
|---|---|---|
| Example 29i[k] | 0.15% Irgafos ® 168[a] 0.15% HALS mixture[m] 0.30% Compound 118 | 3.3 |

For footnotes a), i), k) and m) see the end of Table 23.

EXAMPLE 30

Stabilizing Polypropylene in the Case of Multiple Extrusion and at Especially High Temperatures 1.5 kg of polypropylene powder (Profax®6501), which has been initially stabilized with 0.008% of Irganox®1076 (n-octadecyl 3-[3,5-di-tert-butyl-4-hydroxyphenyl]propionate) (with a melt index of 3.2 measured at 230° C. and under 2.16 kg), are mixed with 0.10% of calcium stearate and 0.015 to 0.20% of the stabilizers listed in Table 14. This mixture is extruded in an extruder having a barrel diameter of 20 mm and a length of 400 mm at 100 revolutions per minute, the maximum extruder temperature being set at 280, 300, 320 and 340° C. For cooling, the extrudate is drawn through a water bath and then granulated. These granules are extruded repeatedly. After 5 extrusions, the melt index is measured (at 230° C. under 2.16 kg). A large increase in the melt index denotes severe chain breakdown and hence poor stabilization. The results are summarized in Table 14.

TABLE 14

| Example | Stabilizers | Amount (% by wt.) | Melt index after 5 extrusions |
|---|---|---|---|
| Example 30a[j] | Irgafos ® 168[a] Irganox ® 1010[f] Chimassorb ® 944[f] | 0.10 0.10 0.20 | 18.3 |
| Example 30b[k] | Compound 108 Irgafos ® 168[a] Irganox ® 1010[f] Chimassorb ® 944[f] | 0.015 0.10 0.05 0.10 | 8.6 |
| Example 30c[k] | Compound 108 Irgafos ® 168[a] Irganox ® 1010[f] Chimassorb ® 119[g] | 0.015 0.10 0.05 0.10 | 8.5 |

For footnotes a), f), g), i), k) and l) see the end of Table 23.

EXAMPLE 31

Stabilization of Polycarbonate 1.0 kg of a polycarbonate powder which has been dried for 8 hours at 120° C. in a vacuum drying oven (Lexan®115, of General Electric) and 0.1 to 0.6 g (0.01 to 0.06%) of the stabilizers listed in Table 15 are mixed for 2 minutes in a Henschel mixer. This mixture is then extruded in a Schwabenthan extruder at a maximum of 280° C. The polymer string is then granulated. Using an injection moulding machine, plates having a layer thickness of 2 mm are then moulded from the granulate so obtained at a maximum of 300° C. These plates are then aged in a circulating air oven at 135° C. for 2000 hours. The yellowness index (YI) of these plates is then determined according to ASTM D 1925-70 and the transmission is determined in percent at 450 nm. Low YI values denote little discoloration, high YI values high discoloration of the patterns. The less discoloration, the more effective the stabilizer. The higher the transmission values, the more effective the stabilizer. The results are compiled in Tables 15 and 16.

TABLE 15

| Example | Stabilizers | Yellowness index prior to oven-ageing | Yellowness index after 2000 hours at 135° C. |
|---|---|---|---|
| 31a[i] | — | 4.3 | 25.5 |
| 31b[i] | 0.05% Irgafos ® 168[a] | 3.4 | 22.7 |
| 31c[k] | 0.01% Compound 103 | 3.4 | 16.6 |
| 31d[k] | 0.01% Compound 107 | 3.4 | 15.1 |
| 31e[k] | 0.05% Irgafos ® 168[a] 0.01% Compound 103 | 3.4 | 15.2 |
| 31f[k] | 0.05% Irgafos ® 168[a] 0.01% Compound 107 | 3.3 | 15.1 |

TABLE 16

| Example | Stabilizers | Transmission in % prior to oven-aging | Transmission in % after 2000 hours at 135° C. |
|---|---|---|---|
| 31a[i] | — | 84.3 | 76.4 |
| 31b[i] | 0.05% Irgafos ® 168[a] | 84.5 | 77.8 |
| 31c[k] | 0.01% Compound 102 | 85.6 | 81.6 |
| 31d[k] | 0.01% Compound 109 | 85.6 | 81.9 |
| 31e[k] | 0.05% Irgafos ® 168[a] 0.01% Compound 102 | 85.8 | 81.5 |
| 31f[k] | 0.05% Irgafos ® 168[a] 0.01% compound 109 | 85.8 | 81.6 |

For footnotes a), i) and k) see the end of Table 23.

EXAMPLE 32

Stabilization of Polycarbonate 1.0 kg of a polycarbonate powder which has been dried for 8 hours at 120° C. in a vacuum drying oven (Lexan®145, of General Electric) is charged with the stabilizers listed in Table 17 and is mixed for 2 minutes in a Henschel mixer. This mixture is then extruded in a Schwabenthan extruder at a maximum of 280° C. The polymer string is then granulated. Using an injection moulding machine, plates having a layer thickness of 2 mm are then moulded from the granulate so obtained at a maximum of 300° C. These plates are then aged in a circulating air oven at 135° C., the time in hours until the yellowness index (YI) reaches a value of 20 according to ASTM D 1925-70 being measured. The longer the time, the more effective the stabilizer. The results are compiled in Table 17.

TABLE 17

| Example | Stabilizers | Time in hours at 135° C. to YI = 20 |
|---|---|---|
| 32a[i] | — | 1550 |
| 32b[i] | 0.05% Irgafos ® 168[a] | 1990 |
| 32c[k] | 0.006% Compound 108 0.022% Irgafos ® 168[a] 0.012% Irganox ® 1076[n] | 2340 |
| 32d[k] | 0.009% Compound 108 0.034% Irgafos ® 168[a] 0.017% Irganox ® 1076[n] | 2355 |

For footnotes a), i), k) and n) see the end of Table 23.

EXAMPLE 33

Stabilisation of Polybutylene Terephthalate (PBT)

1.0 kg of a polybutylene terephthalate powder which has been dried for 10 hours at 100° C. in a vacuum drying oven (Crastin®S600, of Ciba Specialty Chemicals Inc.) is charged with the stabilizers listed in Table 18 and is mixed for 2 minutes in a Henschel mixer. This mixture is then extruded in a twin-screw extruder (type Berstorff) at a maximum of 250° C. and is then granulated. In an injection moulding apparatus, the granulate so obtained is moulded at a maximum of 260° C. to little rods 4×6 mm thick and 50 mm long. These little rods are then aged in a circulating air oven at 160° C. After 360 hours the impact strength of the rods is measured in KJ/m$^2$. The higher the values, the better the stabilization. The results are compiled in Table 18.

TABLE 18

Impact strength in the oven-ageing test at 160° C.

| | | Impact strength in KJ/m$^2$ | |
|---|---|---|---|
| Example | Stabilizers | after 0 h | after 360 h |
| 33a[i] | — | 130 | 27 |
| 33b[i] | 0.05% Irganox ® 245[o] | 131 | 110 |
| 33c[i] | 0.10% Irganox ® 245[o] | 134 | 113 |
| 33d[i] | 0.05% Irganox ® 245[o] 0.05% Irgafos ® 168[a] | 134 | 111 |
| 33e[k] | 0.05% Irganox ® 245[o] 0.05% Irgafos ® 168[a] 0.02% compound 107 | 134 | 132 |

For footnotes a), i), k) and o) see the end of Table 23.

EXAMPLE 34

Stabilization of Polycarbonate 1.0 kg of a polycarbonate powder which has been dried for 8 hours at 120° C. in a vacuum drying oven (Lexan®145, of General Electric) is charged with the stabilizers listed in Table 19 and is mixed for 2 minutes in a Henschel mixer. This mixture is then extruded in a Schwabenthan extruder at a maximum of 280° C. The polymer string is then granulated. Using an injection moulding machine, plates having a layer thickness of 2 mm are then moulded from the granulate so obtained at a maximum of 300° C. These plates are then irradiated in a Weather-O-Meter (WOM CI 65) for 2500 hours at a black standard temperature of 63° C., at a dry/wet cycle of 102/18 minutes and at an intensity of 0.35 W/m$^2$ at 340 nm. The yellowness index (YI) of these plates is then determined according to ASTM D 1925-70. Low YI values denote little discoloration, high YI values high discoloration of the plates. The less discoloration, the more effective the stabilizer or the stabilizer mixture. The results are compiled in Table 19.

TABLE 19

| Example | Stabilizers | Yellowness index after 2500 h exposure to light |
|---|---|---|
| 34a[i] | — | 30.5 |
| 34b[i] | 0.30% Tinuvin ® 234[p] | 17.9 |
| 34c[i] | 0.30% Tinuvin ® 360[q] | 16.8 |
| 34d[i] | 0.30% Tinuvin ® 1577[r] | 11.4 |
| 34e[k] | 0.30% Tinuvin ® 234[p] 0.02% Compound 103 | 15.9 |

TABLE 19-continued

| Example | Stabilizers | Yellowness index after 2500 h exposure to light |
|---|---|---|
| 34f[k] | 0.30% Tinuvin ® 360[q] 0.02% Compound 103 | 14.9 |
| 34g[k] | 0.30% Tinuvin ® 1577[r] 0.02% Compound 103 | 9.2 |
| 34h[k] | 0.30% Tinuvin ® 234[p] 0.05% Irgafos ® 168[a] 0.02% Compound 103 | 13.1 |
| 34i[k] | 0.30% Tinuvin ® 360[q] 0.05% Irgafos ® 168[a] 0.02% Compound 103 | 11.9 |
| 34j[k] | 0.30% Tinuvin ® 1577[r] 0.05% Irgafos ® 168[a] 0.02% Compound 108 | 9.0 |

For footnotes a), i), k), p), q) and r) see the end of Table 23.

EXAMPLE 35

Stabilization of Polycarbonate 1.0 kg of a polycarbonate powder which has been dried for 8 hours at 120° C. in a vacuum drying oven (Lexan®145, of General Electric) is charged with the stabilizers listed in Table 20 and is then mixed for 2 minutes in a Henschel mixer. This mixture is then extruded in a Schwabenthan extruder at a maximum of 280° C. The polymer string is then granulated. The granulate so obtained is packed into 1 cm thick polystyrene boxes and the yellowness index (YI) is determined according to ASTM D 1925-70. Low YI values denote little discoloration, high YI values high discoloration of the samples. The less discoloration, the more effective the stabilizer or the stabilizer mixture. The results are compiled in Table 20.

TABLE 20

| Example | Stabilizers | Yellowness index |
|---|---|---|
| 35a[i] | — | 10.4 |
| 35b[i] | 0.05% GSY ® P101[s] | 5.6 |
| 35c[k] | 0.04% GSY ® P101[s] 0.02% Compound 108 | 2.1 |

For footnotes i), k) and s) see the end of Table 23.

EXAMPLE 36

Stabilization of Polyesters 2.5 kg of a polyester which has been dried for 12 hours at 120° C. in a vacuum drying oven (Polyclear® T86, of Hoechst) is charged with the stabilizers listed in Table 21 and is mixed for 2 hours in a Henschel mixer. This mixture is then extruded in a Schwabenthan extruder at a maximum of 275° C. The polymer string is then granulated. The granulate so obtained is dried for another 12 hours in a vacuum drying oven. In a double determination, 500 mg of the granulate is heated over 10 minutes to 290° C. and is stored for 1 hour under pure oxygen in a rancimate at 290° C. The resulting gaseous separation products are continuously led into an aqueous collecting solution and the conductivity (µS) of this solution is continuously measured. Low conductivity values signify that few separation products are formed, high conductivity values signify that very many separation products are formed. The lower the conductivity values, the more effective the stabilizer. The results are compiled in Table 21.

TABLE 21

| Example | Stabilizers | Conductivity (μS) |
|---|---|---|
| 36a[i] | — | 49 |
| 36b[k] | 0.20% Compound 107 | 35 |

For footnotes i) and k) see the end of Table 23.

EXAMPLE 37

Stabilization of Light-Colored SBR-Vulcanisate

Ozone Atmosphere for 48 Hours 100 parts by weight of Cariflex®S-1502 (styrene/butadiene rubber, Shell) are processed at 60° C., in a mixing mill, with 30.0 parts by weight of Kronos®CL 220 [titanium dioxide (pigment), Kronos Titan GmbH], 30.0 parts by weight of Aktisil®MM [kaolin (filler), Hoffmann Mineral, Neuburg/Donau], 5.0 parts by weight of Naftolen®N 401 [plasticizer, Metaligesellschaft], 10.0 parts by weight of zinc oxide [vulcanization activator], 2.0 parts by weight of stearic acid [vulcanization activator], 2.0 parts by weight of sulfur [vulcanizing agent], 1.0 part by weight of Vulkacit®MOZ [vulcanisation accelerator, Bayer], 0.25 part by weight of Vulkacit®Thiuram [vulcanization accelerator, Bayer] and 1.0 part by weight of the stabilizer to be tested according to Table 22, to form a homogeneous mixture, the vulcanization system (sulfur, Vulkacit®MOZ and Vulkacit®Thiuram) not being added until the end of the mixing process. The mixture is vulcanized in electrical vulcanization presses at 150° C. until T95 is reached in the rheometer curves to form elastomer plates 2 mm thick, 21 cm long and 8.0 cm wide.

Some of the elastomer plates so obtained are tested for the action of ozone according to the ASTM standard D 3395-86 while subject to dynamic elongation. In this test, the plates are first stored for 30 days in a standard atmosphere [23/50 SN-ISO 291]. Test specimens measuring 20 cm by 1 cm are then punched out and exposed to an ozone atmosphere for 48 hours (ozone content: 50 pphm; temperature: 40° C.; humidity: 50% rel.; elongation: 0 to 25%; elongation rate: 0.5 Hz; number of load cycles: approximately 173 000). The test plates are then assessed for crack formation according to ASTM D 3395-86. Grade 0 denotes no cracks; grade 1 denotes narrow flat cracks; grade 2 denotes moderately broad, moderately deep cracks, clearly visible; grade 3 denotes broad and deep cracks. The lower the grade number, the better the stabilization of the elastomer plates. The results are compiled in Table 22.

The remaining elastomer plates are stored for 3 weeks at room temperature in a standard laboratory atmosphere in diffuse daylight. The ΔL-color of those plates is then determined according to DIN 6167, which corresponds to a scale of from 0 to 100. No discoloration is indicated by a value of 100. The results are compiled in Table 22.

TABLE 22

| Examples | Stabilizer | Crack formation according to ASTM D 3395-86 | ΔL-color according to DIN 6167 |
|---|---|---|---|
| Example 37a[i] | — | grade 1-2 | 95 |
| Example 37b[j] | 1.0 phr[u] Vulkanox ® 4010[t] | grade 0 | 71 |
| Example 37c[k] | 1.0 phr[u] Compound 107 | grade 0-1 | 96 |

For footnotes i), k), t and u) see the end of Table 23.

EXAMPLE 38

Stabilisation of Light-Colored SBR-Vulcanisate

Ozone Atmosphere for 96 Hours 100 parts by weight of Cariflex®S-1502 (styrene/butadiene rubber, Shell) are processed at 60° C., in a mixing mill, with 30.0 parts by weight of Kronos®CL 220 [titanium dioxide (pigment), Kronos Titan GmbH], 30.0 parts by weight of Aktisil®MM [kaolin (filler), Hoffmann Mineral, Neuburg/Donau], 5.0 parts by weight of Naftolen®N 401 [plasticiser, Metaligesellschaft], 10.0 parts by weight of zinc oxide [vulcanization activator], 2.0 parts by weight of stearic acid [vulcanization activator], 2.0 parts by weight of sulfur [vulcanizing agent], 1.0 part by weight of Vulkacit®MOZ [vulcanization accelerator, Bayer], 0.25 part by weight of Vulkacit®Thiuram [vulcanization accelerator, Bayer] and 1.0 part by weight of the stabilizer to be tested according to Table 23, to form a homogeneous mixture, the vulcanization system (sulfur, Vulkacit®MOZ and Vulkacit®Thiuram) not being added until the end of the mixing process. The mixture is vulcanized in electrical vulcanization presses at 150° C. until T95 is reached in the rheometer curves to form elastomer plates 2 mm thick, 21 cm long and 8.0 cm wide.

Some of the elastomer plates so obtained are tested for the action of ozone according to the ASTM standard D 3395-86 while subject to dynamic elongation. In this test the plates are first stored for 30 days in a standard atmosphere [23/50 SN-ISO 291]. Test specimens measuring 20 cm by 1 cm are then punched out and exposed to an ozone atmosphere for 96 hours (ozone content: 50 pphm; temperature: 40° C.; humidity: 50% rel.; elongation: 0 to 25%; elongation rate: 0.5 Hz; number of load cycles: approximately 173 000). The test plates are then assessed for crack formation according to ASTM D 3395-86. Grade 0 denotes no cracks; grade 1 denotes narrow flat cracks; grade 2 denotes moderately broad, moderately deep cracks, clearly visible; grade 3 denotes broad and deep cracks. The lower the grade number, the better the stabilization of the elastomer plates. The results are compiled in Table 23.

The remaining elastomer plates are stored for 3 weeks at room temperature in a standard laboratory atmosphere in diffuse daylight. The ΔL-color of those plates is then determined according to DIN 6167, which corresponds to a scale of from 0 to 100. No discoloration is indicated by a value of 100. The results are compiled in Table 23.

TABLE 23

| Examples | Stabilizer | Crack formation according to ASTM D 3395-86 | ΔL-color according to DIN 6167 |
|---|---|---|---|
| Example 38a[i] | — | grade 2 | 97 |
| Example 38b[j] | 2.0 phr[u] Vulkanox ® 4010[t] | grade 0 | 56 |
| Example 38c[k] | 2.0 phr[u] Compound 103 | grade 1 | 94 |
| Example 38d[k] | 2.0 phr[u] Compound 114 | grade 1 | 94 |
| Example 38e[k] | 2.0 phr[u] Compound 117 | grade 1 | 95 | a) Irgafos®168 (Ciba Specialty Chemicals Inc.) is tris(2,4-di-tert-butylphenyl)phosphite.
b) Sandostab®P-EPQ (Clariant) is tetrakis(2,4-di-tert-butylphenyl)-4,4'-biphenylene diphosphonite.
c) Irganox®5057 (Ciba Specialty Chemicals Inc.) is a secondary amine antioxidant and is a technical mixture, obtained by reaction of diphenylamine with diisobutylene, comprising a') 3% of diphenylamine;
b') 14% of 4-tert-butyldiphenylamine;
c') 30% of compounds of the group
  i) 4-tert-octyldiphenylamine,
  ii) 4,4'-di-tert-butyldiphenylamine,
  iii) 2,4,4'-tris-tert-butyldiphenylamine;
d') 29% of the compounds of the group
  i) 4-tert-butyl-4'-tert-octyldiphenylamine,
  ii) o,o'-, m, m'- or p, p'-di-tert-octyldiphenylamine,
  iii) 2,4-di-tert-butyl-4'-tert-octyldiphenylamine;
e') 24% of the compounds of the group
  i) 4,4'-di-tert-octyldiphenylamine and
  ii) 2,4-di-tert-octyl-4'-tert-butyldiphenylamine.
d) Irganox®1135 (Ciba Specialty Chemicals Inc.) is a phenolic antioxidant of the formula A-1.

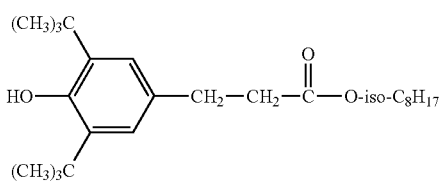

(A-1)

e) Tinuvin®622 (Ciba Specialty Chemicals Inc.) is a compound of the formula H1 in which the average molecular weight is about 3000.

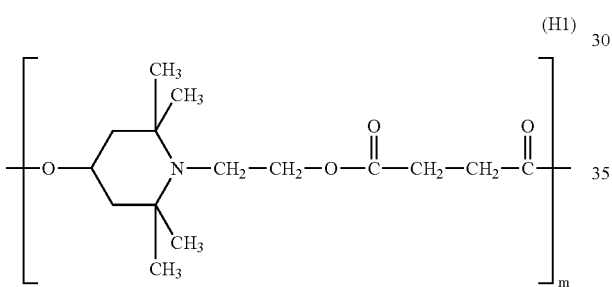

(H1)

f) Chimassorb®944 (Ciba Specialty Chemicals Inc.) denotes linear or cyclic condensation products prepared from N,N'-bis(2,2,6,6-tetramethyl-4-piperidyl)hexamethylendiamine and 4-tert-octylamino-2,6-dichloro-1,3,5-triazine and is a compound of the formula H2 in which the average molecular weight is about 2500.

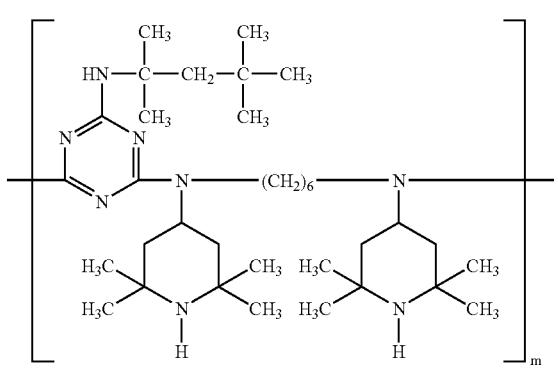

(H2)

g) Chimassorb®119 (Ciba Specialty Chemicals Inc.) denotes condensation products prepared from 2-chloro-4,6-di(4-n-butylamino-1,2,2,6,6-pentamethylpiperidyl)-1,3,5-triazine and 1,2-bis(3-aminopropylamino)ethane and is a compound of the formula H3

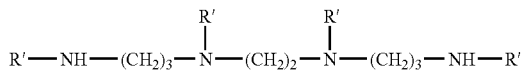

(H3)

in which R' =

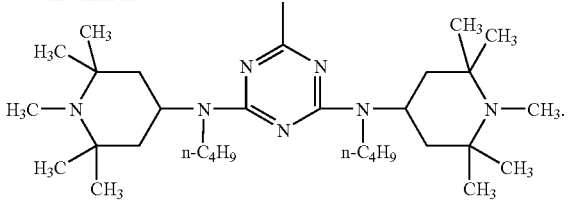

h) Irgafos®38 (Ciba Specialty Chemicals Inc.) is a compound of the formula P-1.

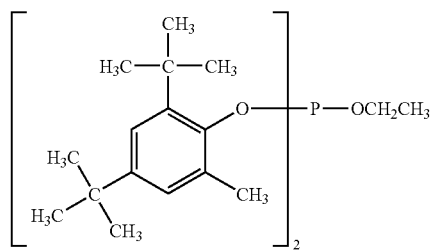

(P-1)

i) Comparison Example.
k) Example of this invention.
l) Irganox®1010 (Ciba Specialty Chemicals Inc.) denotes the pentaerythritol ester of 3-(3,5-di-tert-butyl-4-hydroxyphenyl)propionic acid.
m) HALS mixture is a 1:1 mixture of Tinuvin®622 [Ciba Specialty Chemicals Inc.; see footnote e)] and Chimassorb®119 (Ciba Specialty Chemicals Inc.; see footnote g)].
n) Irganox®1076 (Ciba Specialty Chemicals Inc.) denotes a compound of formula A-2.

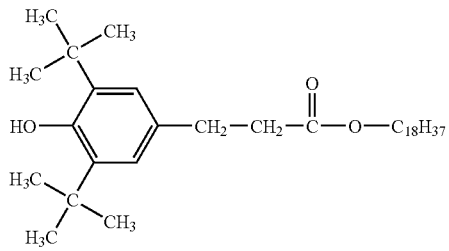

(A-2)

o) Irganox®245 (Ciba Specialty Chemicals Inc.) denotes compound of formula A-3.

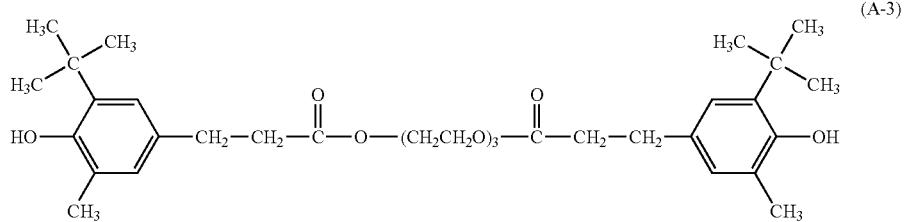
(A-3)

p) Tinuvin®234 (Ciba Specialty Chemicals Inc.) denotes a compound of formula UV-1.

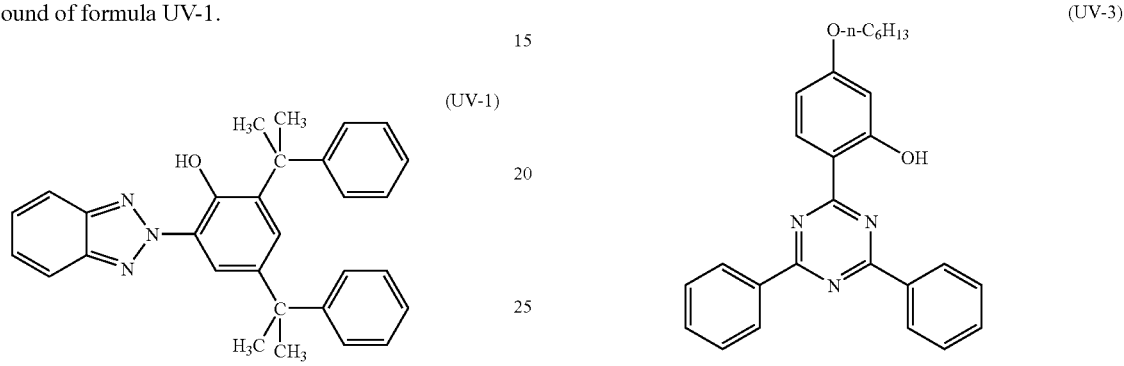

s) GSY® P101 (Yoshitomi) denotes a compound of formula P-2.

q) Tinuvin®360 (Ciba Specialty Chemicals Inc.) denotes a compound of formula UV-2.

t) Vulkanox®4010 (Bayer) denotes 4-isopropylamino-diphenylamine of formula A.

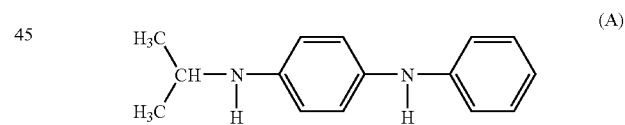

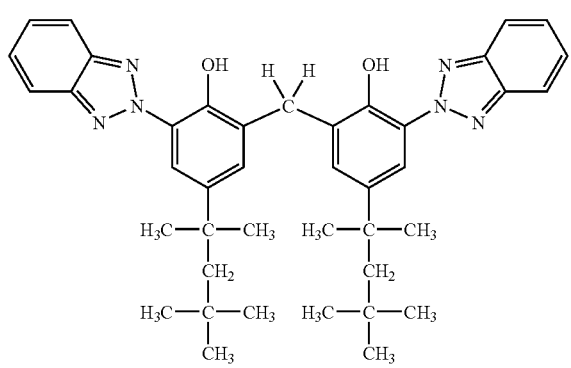

r) Tinuvin®1577 (Ciba Specialty Chemicals Inc.) denotes a compound of formula UV-3.

u) phr denotes "parts per hundred of rubber".

What is claimed is:

1. A composition comprising
   a) a natural, semisynthetic or synthetic polymer and
   b) at least one compound of formula

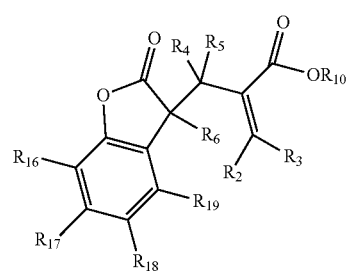

wherein $R_{10}$ is hydrogen or $C_1$-$C_{25}$alkyl, $R_2$ and $R_3$ are hydrogen, $R_4$ and $R_5$ are hydrogen, $R_6$ is unsubstituted or $C_1$-$C_4$alkyl-substituted phenyl and $R_{16}$ and $R_{18}$ are $C_1$-$C_{25}$alkyl and $R_{17}$ and $R_{19}$ are hydrogen.

2. A composition according to claim 1, wherein
$R_{10}$ is hydrogen or $C_1$-$C_{12}$alkyl and
$R_{16}$ and $R_{18}$ are $C_1$-$C_{18}$alkyl.

3. A composition according to claim 1, wherein
$R_{10}$ is hydrogen or $C_1$-$C_8$alkyl and
$R_{16}$ and $R_{18}$ are $C_1$-$C_{12}$alkyl.

4. A composition according to claim 1, wherein
$R_{10}$ is hydrogen or $C_1$-$C_4$alkyl and
$R_{16}$ and $R_{18}$ are $C_1$-$C_4$alkyl.

5. A composition according to claim 1, comprising as component (a) a thermoplastic polymer.

6. A composition according to claim 1, comprising as component (a) a polyolefin.

7. A composition according to claim 1, in which component (b) is present in an amount of from 0.0005 to 10% based on the weight of component (a).

8. A composition according to claim 1, comprising further additives.

9. A composition according to claim 8, comprising as further additives phenolic antioxidants, light-stabilizers and/or processing stabilizers.

10. A compound of formula

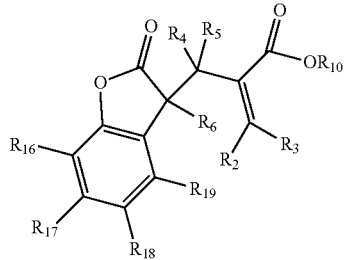

wherein $R_{10}$ is hydrogen or $C_1$-$C_{25}$alkyl, $R_2$ and $R_3$ are hydrogen, $R_4$ and $R_5$ are hydrogen, $R_6$ is unsubstituted or $C_1$-$C_4$alkyl-substituted phenyl and $R_{16}$ and $R_{18}$ are $C_1$-$C_{25}$alkyl and $R_{17}$ and $R_{19}$ are hydrogen.

11. A compound according to claim 10, wherein $R_6$ is phenyl, $R_{10}$ is hydrogen or $C_1$-$C_4$alkyl and $R_{16}$ and $R_{18}$ are $C_1$-$C_4$alkyl.

12. A process for stabilizing a natural, semisynthetic or synthetic polymer against oxidative, thermal or light-induced degradation, which process comprises incorporating therein or applying thereto at least one compound of formula

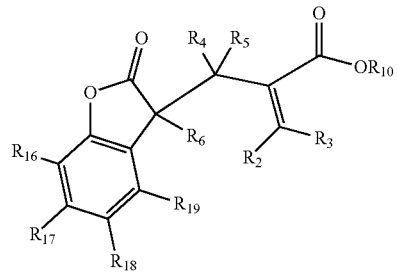

wherein $R_{10}$ is hydrogen or $C_1$-$C_{25}$alkyl, $R_2$ and $R_3$ are hydrogen, $R_4$ and $R_5$ are hydrogen, $R_6$ is unsubstituted or $C_1$-$C_4$alkyl-substituted phenyl and $R_{16}$ and $R_{18}$ are $C_1$-$C_{25}$alkyl and $R_{17}$ and $R_{19}$ are hydrogen.

* * * * *